United States Patent
Goodman et al.

(10) Patent No.: US 6,316,153 B1
(45) Date of Patent: Nov. 13, 2001

(54) FREE-FORM FABRICATON USING MULTI-PHOTON EXCITATION

(75) Inventors: Steven L. Goodman, Madison, WI (US); Paul Campagnola, Simsbury, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 09/295,992

(22) Filed: Apr. 21, 1999

Related U.S. Application Data

(60) Provisional application No. 60/082,575, filed on Apr. 21, 1998, and provisional application No. 60/112,797, filed on Dec. 18, 1998.

(51) Int. Cl.[7] .................................................. G03C 5/00
(52) U.S. Cl. ..................... 430/8; 430/270.1; 430/281.1; 430/311; 430/320; 609/88; 609/89
(58) Field of Search .................... 607/88, 89; 430/270.1, 430/281.1, 311, 320, 5, 8

(56) References Cited

U.S. PATENT DOCUMENTS

| | | |
|---|---|---|
| 4,575,330 | 3/1986 | Hull . |
| 5,034,613 | 7/1991 | Denk et al. . |
| 5,113,117 | 5/1992 | Brooks et al. . |
| 5,289,407 | 2/1994 | Strickler et al. ..................... 365/106 |
| 5,360,764 | 11/1994 | Celotta ................................ 437/173 |
| 5,370,692 | 12/1994 | Fink et al. . |
| 5,380,589 | 1/1995 | Goodman et al. . |
| 5,410,016 | 4/1995 | Hubbell et al. ....................... 528/354 |
| 5,518,680 | 5/1996 | Cima et al. . |
| 5,556,752 | 9/1996 | Lockhart et al. . |
| 5,700,241 | 12/1997 | Goodman . |
| 5,808,256 | 9/1998 | Kira et al. ......................... 204/157.15 |
| 5,849,035 | 12/1998 | Pathak et al. ............................ 623/1 |
| 5,858,746 | 1/1999 | Hubbell et al. ....................... 435/177 |
| 5,998,597 | * 12/1999 | Fisher et al. ......................... 536/23.1 |

FOREIGN PATENT DOCUMENTS

| | | |
|---|---|---|
| 4309068 | 9/1994 | (DE) . |
| 19628355 | 3/1997 | (DE) . |

OTHER PUBLICATIONS

Cima, L. G., et al, "Solid Free Form Fabrication of Polymer Devices for Tissue Engineering and Drug Delivery", 21st Annual Meeting of the Society for Biomaterials, Mar. 18–22, 1996, San Francisco, California.
Cumpston, Brian H., et al, "Two–photon polymerization initiators for three–dimensional optical data storage and microfabricaton", *Nature*, vol. 398, pp. 51–54, Mar. 4, 1999.
Lieberman, K, et al, "A Light Source Smaller Than the Optical Wavelength", *Science*, vol. 247, pp. 59–61, Jan. 5, 1990.
Maruo, Shoji, et al, "Three–dimensional microfabrication with two–photon–absorbed photopolymerization", *Optics Letters*, vol. 22, No. 2, pp. 132–134, Jan. 15, 1997.

Hell, Stefan et al, Fundamental improvement of resolution with 4Pi–confocal fluorescence microscope using two–photon excitation, *Optics Communication*, 93 pp. 277–282 (1992).
Kawata, Yoshimasa, et al, "Use of two–photon absorption in a photorefractive crystal for three–dimensional optical memory", *Optics Letters*, vol. 23, No. 10, pp. 756–758, May 15, 1998.
Lewis, Michael K, et al, "Near–field scanning optical microscopy of single molecules by femtosecond two–photon excitation", *Optics Letters*, vol. 23, No. 14, pp. 1111–1113, Jul. 15, 1998.
Hell, Stefan W., et al, "Two–Photon near–and far–field fluorescence microscopy with continuous–wave excitation", *Optics Letters*, vol. 23, No. 15, pp. 1238–1240, 1998.
Bhawalker, J. D., Ph.D., et al, "Two–Photon Photodynamic Therapy", *Journal of Clinical Laser Medicin & Surgery*, vol. 15, No. 5, pp. 201–204 (1997).
Witzgall, George, et al, "Single–shot two–photon exposure of commercial photoresist for the production of three–dimensional structures", *Optical Letters*, vol. 23, No. 22, pp. 1745–1747, Nov. 15, 1998.
Watanabe, Tsuyoshi, et al., "Development of High Precision Solid Creation System", Radtech Asia '93 UV/EB Conference Exposition Conference Proceedings, Nov. 10–13, 1993, pp. 462–467.
Denk, Winfried, "Two–Photon Laser Scanning Fluorescence Microscopy", *Science*, vol. 248, pp. 73–76, Apr. 6, 1990.

(List continued on next page.)

*Primary Examiner*—John A. McPherson
(74) *Attorney, Agent, or Firm*—Cantor Colburn LLP

(57) ABSTRACT

A method wherein small, two- or three- dimensional structures are formed by multiple-photon-absorbed photopolymerization and/or cross-linking of a precursor composition. Use of multi-photon excitation allows fabrication of structures and structural features having at least one dimension of less than about one micron, preferably less than about 500 nm, more preferably less than about 250 nm, and most preferably of less than about 100 nm, in bulk phase as well as in solution, and from a wide variety of organic and inorganic precursor subunits, including synthetic polymers and biological polymers such as proteins, lipids, oligonucleotides, and the like. In one embodiment, use of two-photon far field optics allows the formation of structures having X-Y dimensions of less than about 300 mn and a Z dimension of less than about 500 nm, while use of three-photon far field optics allows the formation of structures having X-Y dimensions of less than about 250 mn and a Z dimension of less than about 300 nm. In a particularly preferred embodiment, use of a 4 pi optical configuration in combination with two-photon far field excitation allows the formation of structures having X-Y dimensions of less than about 150 nm and a Z dimension of less than about 100 mn. In another embodiment, use of multi-photon near field optics results in the formation of structures having X, Y, and Z dimensions of less than about 50 nm. In this embodiment, near field fabrication is achieved by two-photon excitation through fiber probes.

89 Claims, 13 Drawing Sheets

OTHER PUBLICATIONS

Nakamura, O., "Three–dimensional imaging characteristics of laser scan fluorescene microscopy: Two–photon excitation vs. single–photon excitation", *Optik*, vol. 93, No. 1, pp. 39–42 (1993).

Nakamura, O., et al, "A two–photon scanning fluorescence microscope with deep UV excitation and near UV detection", *Optik*, vol 100, No. 4, pp. 167–170 (1995).

Strickler, James H., et al, "Two–photon excitation in laser scanning fluorescence microscopy", *SPIE*, vol. 1398 CAN–AM Eastern '90, pp. 107–118.

En S. Wu, James H. Strickler, William R. Harrell, and Watt W. Webb, "Two–Photon Lithography for Microelectronic Application", SPIE vol. 1674 Optical/Laser Microlithography V (1992), pp. 776–782.

\* cited by examiner

FLUID FLOW OR STAGE TRANSLATION

FREE-FORM FABRICATON USING MULTI-PHOTON EXCITATION

CROSS-REFERENCE TO RELATED APPLICATIONS

This application claims priority to U.S. provisional patent application Ser. No. 60/082,575, filed Apr. 21, 1998, and U.S. patent application Ser. No. 60/112,797, filed Dec. 18, 1998, both of which are incorporated by reference herein in their entireties.

BACKGROUND OF THE INVENTION

1. Field of the Invention

This invention relates generally to methods of forming nanoscale structures and the nanoscale structures formed thereby. In particular, this invention relates to methods using multi-photon excitation for the fabrication of structures with nanometer-level precision.

2. Description of the Related Art

Three-dimensional objects having fine-scale microstructures possess unique and technologically attractive properties. There has been particular interest recently in the fabrication of structures with nanometer-level precision, that is, objects with structures or structural features measurable in the nanometer range. Such nanoscale structures have dimensions or features in the range of about 2 to about 100 nm (nanometer, wherein 1 nm=10 angstroms), which is on the order of the size of macromolecules such as proteins and protein complexes.

Photolithography, including methods using X-ray and deep UV, is well-known for producing two-dimensional structures with small-scale features. However, this technique does not allow the production of complex, curved three-dimensional surfaces, as it is very limited in the complexity achievable in the z-direction. Three-dimensional objects produced by photolithographic methods have therefore been essentially limited to columnar structures. Objects with features smaller than 150 nm are not readily producible or routinely available. George M. Whitesides has also described several methods for micro-scale fabrication based on microcontact printing and modification of surface chemistry with self-assembled monolayers. These methods, however, are also very limited in the ability to build in the third dimension, as well as in their chemistry. A method for manufacturing three-dimensional optical data storage and retrieval structures by reaction of polyesters using two-photon excitation is disclosed in U.S. Pat. No. 5,289,407 to Strickler, et al., which is incorporated herein by reference in its entirety.

A number of other, different approaches have been described for the synthesis of three-dimensional objects with small-scale features, for example biomimetic matrix topographies such as basement membrane textures. As described in U.S. Pat. No. 5,700,241, such structures are produced by removal of epithelial or endothelial cell layers to expose the supporting basement membrane or matrix. The exposed topography is then used as a mold for polymer casting. The surface of the resultant molded negative replica of the matrix topography is then itself cast with the final (bio)material of choice. With this methodology, three-dimensional bionminetic matrices can be prepared for both experimental investigations into cellular biology, and to potentially improve the cell and tissue response to implanted biomaterials. Although this method can produce very complex three-dimensional topography, it does not provide for topographic design flexibility, since all constructs must begin with a biological surface. In addition, while many materials may be used for fabrication, the procedure does not provide for spatial control of chemistry.

Scanning tunneling microscopy has also been used to move atoms on surfaces. However, this technique is extremely limited in the sizes and chemistry of the fabricated region. Another technique which has been described for the solid, free-form fabrication of microscale structures includes forming successive, adjacent, cross-sectional laminae of the object at the surface of a fluid medium or other bed, the successive laminae being automatically integrated as they are formed to define the desired three-dimensional object, as disclosed in U.S. Pat. No. 4,575,330 to Hull. U.S. Pat. No. 5,518,680 to Cima et al. similarly discloses successive printing of layers of powder in a solvent which causes binding of the successive layers, thereby allowing the formation of drug delivery devices having thicknesses on the order of about 100 microns.

Three-dimensional objects have also been generated by selective curing of a reactive fluid medium by a beam or beams of ultraviolet (UV) radiation brought to selective focus at prescribed intersection points within the three-dimensional volume of the fluid medium. Disadvantages of such systems include the use of UV radiation, which requires expensive and cumbersome optics and lens, as well as the associated poor focusing qualities of excimer and other UV laser sources.

An additional technique for generating three-dimensional microscale objects is described by S. Maruo, O. Nakamura, and S. Kawata et al. in "Three Dimensional Microfabrication With Two-Photon-Absorbed Photopolymerization", Optics Letters, Vol. 22, No. 2, pp. 132–134 (1997), which is incorporated herein by reference in its entirety. Maruo et al. discloses that microscale structures are formed by subjecting urethane acrylate monomers and oligomers to near-irfrared laser light in a non-solvent system. Use of two-photon absorption for initiation of the reaction leads to a spiral wire having a diameter of 6 microns, an axial pitch of 10.3 micron, and a width of nearly 1.3 microns. While small, such structures are not in the nanoscale region. Maruo et al. furthermore only describe synthesis in a non-solvent system, which is incompatible with most biomolecules.

Accordingly, there stiff remains a need for methods of free-form fabrication of two- and three-dimensional structures having dimensions or features in the micron and nanometer range, especially techniques suitable for synthesis using biomolecular subunits such as proteins, peptides, oligonucleotides, as well as bio-active small molecules such as hormones, cytokines and drugs.

SUMMARY OF THE INVENTION

The above-discussed and other drawbacks and deficiencies of the prior art are overcome or alleviated by the method and apparatus of the present invention, wherein small, two- or three- dimensional structures are formed by multiple-photon-absorbed photopolymerization and/or cross-linning of a precursor composition, that is, photopolymerization using multi-photon excitation. Use of multi-photon excitation allows fabrication of structures and structural features having at least one dimension of less than about one mincron, preferably less than about 500 nm, more preferably less than about 250 nm, and most preferably of less than about 100 nm, in bulk phase as well as in solution, and from a wide variety of organic and inorganic precursor subunits, including synthetic polymers and biological polymers such as proteins, lipids, oligonucleotides, and the like.

In one embodiment, use of two-photon far field optics allows the formation of structures having X-Y dimensions of less than about 300 nm and a Z dimension of less than about 500 nm, while use of three-photon far field optics allows the formation of structures having X-Y dimensions of less than about 250 nm and a Z dimension of less than about 300 nm. In a particularly preferred embodiment, use of a 4 pi optical configuration in combination with two-photon far field excitation allows the formation of structures having X-Y dimensions of less than about 150 nm and a Z dimension of less than about 100 nm. In another embodiment, use of multi-photon near field optics results in the formation of structures having X,Y, and Z dimensions of less than about 50 nm. In this embodiment, near field fabrication is achieved by two-photon excitation through fiber probes. In a related embodiment, the optical element of the near field embodiment is coupled with a multiple -barreled pipette for precise delivery of components into multiple areas simultaneously or sequentially.

The method described herein is useful for the formation of a variety of small-scale structures. In one embodiment, noncross-linked agents are entrapped (permanently or temporarily) in a gel or matrix formed by multi-photon excitation. Such gels or matrices may have controlled release, degradation, and/or diffisivity properties. Agents include proteins, peptides, carbohydrates, drugs, enzymes, liposomes, nucleotides, and cells. In a related embodiment, multi-photon excitation is used to fabricate devices having varying cross-link densities and/or chemistries to produce materials having variable degradation properties for use as controlled release devices in drug delivery, biomaterials, tissue engineering, and environmental applications.

In another embodiment, multi-photon excitation is used to modify the surface of biological or conventionally fabricated materials. The materials may have complex surface features, or the present method may be used to provide complex features to the materials to the materials. Exemplary applications include adding one or more bioactive functions to an integrated circuit (IC) chip, manufacturing biomimetic surfaces for use with tissue cell culture, and modified explanted tissue for re-implantation or other uses. The combination of microscopy and multi-photon excitation allows the micro-positioning of one or more features on a surface. In a related embodiment, multi-photon excitation is used to manufacture ciliated surfaces or other micro-sized transport devices using motile proteins.

In another embodiment, multi-photon excitation is used to create structures which, in conjunction with shrinkage or expansion effects, dynamic shape change effects (i.e., Poisson ratio effects), and/or groups active under certain chemical conditions, will result in more complex structures. Such structures may be used as a variable filter or as a small-scale actuator to exert physical force, alter fluid flow, and the like. In a related embodiment optical devices are manufactured in layers and/or in other two- and three-dimensional configurations by configuring optically active and chiral compounds.

In another embodiment, multi-photon excitation is used to provide spatial orientation of enzymes on or within substrates or manufactured constructs. Organization is provided by application of electrostatic fields, selective adsorption, shear forces and by optical and magnetic traps.

In another embodiment, proteins are cross-linked directly, without use of photosensitizers or chemical crosslinking agents.

In another embodiment, multi-photon excitation is used to effect nanofabrication at remote sites via optical fibers. Such optical fibers may be placed, for example inside a catheter. Nanofabrication in this embodiment includes delivery of drugs or other biologically active agents, controlled delivery of tissue engineering scaffolding agents, growth factors, and the like; and minimally invasive assembly of structural elements or devices such as stents.

The method and apparatus of the present invention allows the formation of structures having smaller dimensions than before possible. The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES:

FIGS. 24A and 24C show enzyme-linked fluorescence about 30 minutes apart, and FIG. 24B is a transmitted light image.

DETAILED DESCRIPTION OF THE PREFERRED EMBODIMENTS

In accordance with the present invention, small two- or three-dimensional structures are formed by multiple photon induced polymerization or cross-linking of a precursor composition. For convenience, "structures" and "constructs" as used herein refers both to microscale and nanoscale objects in their entirety, that is, objects having overall X-Y or X-Y-Z dimensions in the micron and nanometer range, as well as larger objects having features with X-Y or X-Y-Z dimensions in the micron and millimeter range. "Multiple photon excitation" as used herein means the simultaneous absorption of multiple photons by a reactive molecule. The method is particularly suitable for the formation of three-dimensional objects or structures having dimensions on the micro- and nanometer scale, that is, structures built up from elements with point volumes having dimensions of less than about 1 micron, preferably elements having at least one dimension of less than about 500 nm, 250 nm, 100 nm, and most preferably less than about 50 nm. The structure geometry will depend on the optical method used for photoexcitation and reaction of the precursors, the movement of the laser and/or stage, and the choice of precursors, as dictated by the desired morphology of the final structure. While the following discussion is directed to laser excitation, it is to be understood that other methods for achieving sufficient photon density are also within the scope of the present invention.

Figure 1:
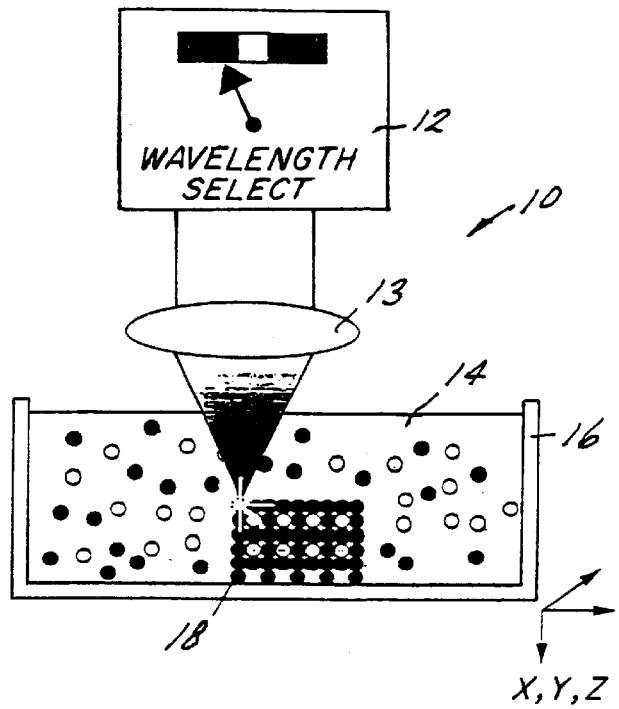
FIG. 1 is a schematic diagram of fabrication using multi-photon excitation as described herein.

As shown schematically in FIG. 1, a photon source, for example pulsed near-IR laser 12 is focused via optics 13 into a precursor composition 14 capable of radiation-induced photopolymerization or cross-lining. In a particularly advantageous feature, precursor composition 14 is an aqueous solution. Precursor composition 14 is placed on stage 16, which may be capable of movement in the X, Y, and/or Z direction. The focused wavelength is an approximately even multiple of that required for photoactivation of the reactive species with linear optics, resulting in multi-photon excitation. Frequently, real, excited states which are normally accessed via single photon absorption may also be excited via absorption of two quanta, each having half the energy of the single photon, or three quanta, each having a third of the energy of the single photon, etc. The multi-photon excited states are often not a precisely even multiple of the wavelength required for the single-photon excited state. Importantly, the photons must impinge simultaneously on the molecule, such that the excitation rate is proportional to the square of the incident intensity. Excitation is therefore confined to the ellipsoidal focal volume where the intensity is extremely high. Thus, two photons, at a wavelength double that required for excitation, or three long wave photons, at a wavelength triple that required for excitation, or even four photons-, at a wavelength quadruple that required for excitation of the reactive species, is used for activation.

The squared or cubed point-spread finction associated with two- or three-photon laser absorption, respectively, results in only a small volume of the reactive species being exposed to the applied radiative energy. Where the photon density is high, molecules at the focal point capable of absorbing a UV or short wave photon absorbs two (or three) near-IR photons at the same time, thereby forming at least one reactive species such as a radical or radical ion. This reactive species then reacts, or propagates via radical- or cation-based chain reactions, until chain termination steps are reached, forming polymerized or cross-linked areas thereby.

Two- or three-dimensional objects 18 are formed by successive movement of the photon beam and/or stage 16 until the desired structure is built point by point. For example, light may be directed onto an X-Y plane by sequential movement of the laser. The stage is then be moved in the Z-direction an appropriate amount, and second, third, and higher X-Y lamellar structures are formed. This method of three-dimensional structure formation is similar to the successive layer formation as described by Cima et al., but allows the formation of structures having smaller features in all three planes. This method is furthermore not limited to this formation sequence, in that any combination of laser/stage movement may be used. Thus, the method of Maruo et al., which discloses only movement of the stage, is limited to formation of structures of greater than 1 micron, possibly because of optics and other conditions, but also possibly because movement of a stage is slower. The fastest volume formation based on stage movement as described by Maruo et al. is approximately 1 pixel per 1, or even 10, milliseconds. Laser movement, on the other hand, is faster, on the order of the formation of 1 pixel per microsecond. Structures of high three-dimensional complexity are thus available, in a shorter period of time.

A number of advantages result from the use of multi-photon excitation in accordance with the present method, notably the ability to probe deeply into a bulk or solution phase sample with an unprecedented degree of control in the x- and y-, as well as z-directions, with only minimal optical effects above and below the focal point. Thus use of multi-photon excitation allows synthesis with various biomolecules, in that infrared, red, deep red, and visible light illumination minimizes damage to proteins, enzymes, or organic molecules adjacent to the focal point, due to the minimal absorbance and scattering of IR and red light compared to UV light. Use of IR and red light also permits fabrication within tissues and through turbid media such as blood. A further advantage is that it is possible to limit the size of a fabricated feature to an area even smaller than the focal point of the photon source, by focusing the activation zone (the area of high proton density) partially within a non-reactive substrate or other location where activation does not occur.

Other advantages are that the deep red, red, infrared, and other visible light optics are less expensive and cumbersome than those required and available for activation using UV radiation. Lasers operated at these wavelengths also provide diffraction limited light sources, unlike conventional UV excimer lasers. A wider range of activation molecules are available (deeper UV) without damage or unwanted side reactions than is possible using UV activation. Fiber optics may be easily used for light transmission, resulting in higher energy, less beam spread, better collimation, and less chromatic spread compared to using UV-associated optics.

Nonlinear optics are presently preferred in the practice of the present invention. There are a number of advantages to use of nonlinear optics in freeform fabrication, one of the most important being that it allows for high energy peak power to be confined to a smaller area than that achievable with linear infrared optics. Practical realization of two-photon laser scanning microscopy is described by W. Denk, J. H. Strickler, and W. W. Webb in Science, Vol. 248, p. 73 (1990), which is incorporated herein by reference. Other uses and descriptions of two-photon excitation are further described by O. Nakamura in Optik, Vol. 93, p. 39 et seq. (1993); by O. Nakamura and T. Okada in Optik, Vol. 100, p. 167 et seq. (1995); by E. S. Wu, J. H. Strickler, W. R. Harrell, and W. W. Webb in Proc. SPIE, Vol. 1398, p. 107 et seq. (1990) and in U.S. Pat. No. 5,289,407 to Strickler and Webb; and by Watanabe, M. Okawa, T. Ukachi, F. Kurihara, and H. Harimaya, In Proceedings of RadTech Asia 1993, p. 462, published by RadTech, Japan (1993), the relevant portions of which preceding references are also incorporated by reference herein. "A Light Source Smaller Than the Optical Wavelength" by K. Liebermann, S. Harush, A Lewis, and R. Kopelman, Science, Vol. 247, pp. 61 (1990) is further incorporated by reference herein.

Figure 2:
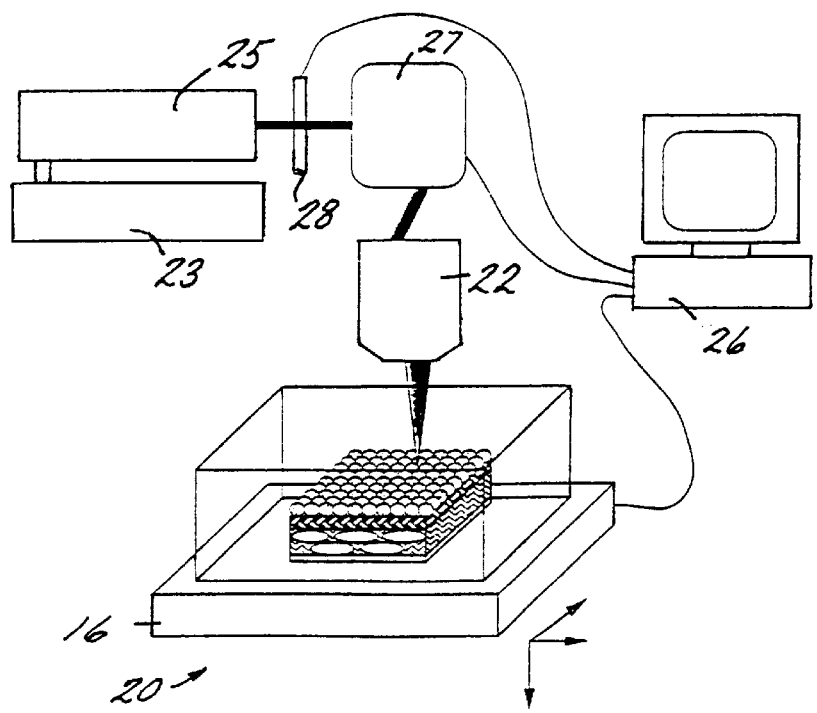
FIG. 2 is a schematic diagram of an apparatus having wide-field optics suitable for fabrication by multi-photon excitation.

In preferred embodiments, use of two-photon wide field (far field) excitation allows the formation of structures comprising individual point volumes with X-Y dimensions of less rs than about 300 nm and optionally a Z dimension of less than about 500 nm, while use of three-photon far field excitation allows the formation of structures comprising individual poit volumes with X-Y dimensions of less than about 250 nm and optionally a Z dimension of less than about 300 nm. A schematic diagram of an apparatus 20 suitable for use with two-photon or three-photon far field (nonlinear) optics is shown in FIG. 2, wherein stage 16 is located beneath a high numerical aperture (A) objective lens 22. PC controller 26 controls both laser shutter 28 and stage 16. A preferred photon source comprises an argon ion pump laser 23 in tandem with a Ti:sapphire laser 25. Optional galvo scanner 27 allows very fine control of the activation zone.

Figure 3:
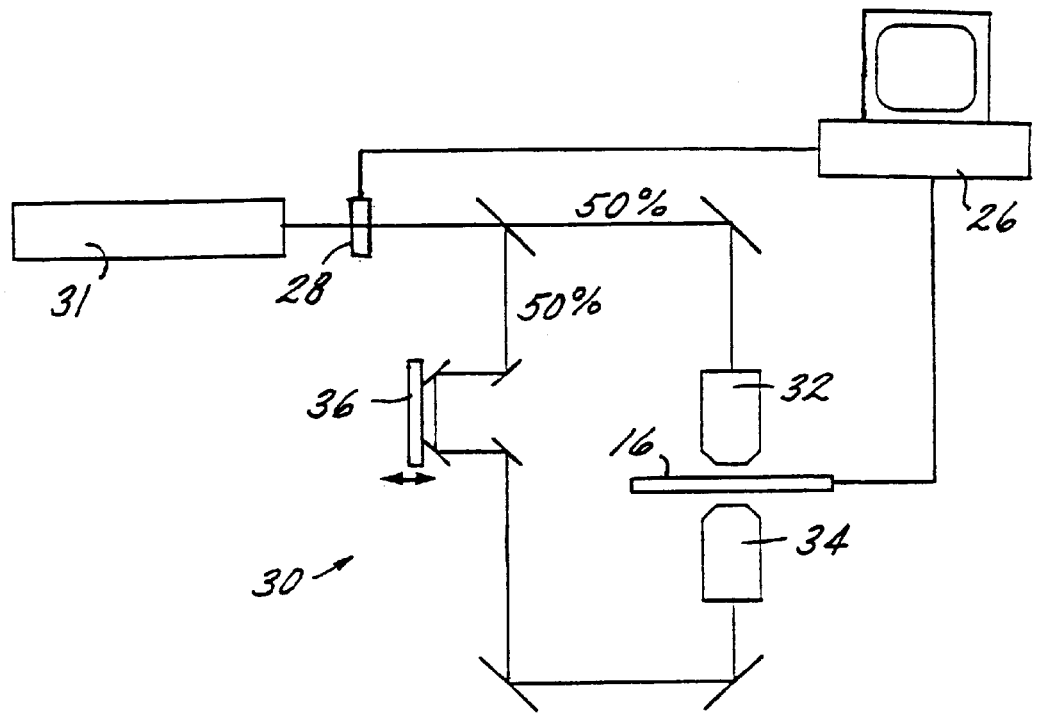
FIG. 3 is a schematic diagram of an apparatus having wide field 4 pi optics suitable for fabrication by multi-photon excitation.

In another preferred embodiment, use of a 4 pi far field optical configuration in combination with two-photon excitation allows the formation of structures comprising individual point volumes having X-Y dimensions of less than about 250 nm and a Z dimension of less than about 100 nm. 4 Pi optics in connection with fluorescence microscopes is described by S. Hell and E. H. K. Stelzer in "Fundamental Improvement of Resolution With a 4 Pi-Confocal Fluorescence Microscope Using Two-Photon Excitation", Optics Communications, Vol. 93, pp. 277–282 (1992), which is incorporated herein by reference in its entirety. The apparatus of FIG. 3 is suitable for practice of this embodiment, comprising photon source 32, two high NA lens 32, 34 located above and below stage 16. A second movable stage 36 allows very fine control of the position of the laser beam to less than optical levels to adjust femtosecond photon pulses to temporarily overlap at the site of fabrication. Use of excitation from objectives both above and below the sample results in improved optical resolution. The two beams are precisely aligned both spatially and temporally, and the power levels are carefully adjusted such that significant excitation does not arise from ether bean alone.

4 Pi optics require objective elements both above and below the sample. The fabrication of tall or thick objects is thus limited by the working distance of the objective elements, at this point to about 200 microns at the highest resolutions. In addition, any supporting material and the item to be fabricated must be transparent at the appropriate visible, red or infrared wavelengths. However, this method also provides the ability to make very small features with excellent spatial precision very quickly, due to high photon densities at the mutual focal point of the two objective lens elements. This embodiment is thus particularly useful for the production of thin objects with complex features, such as masks for photolithography, coatings, membranes, and sensors.

Figure 4:
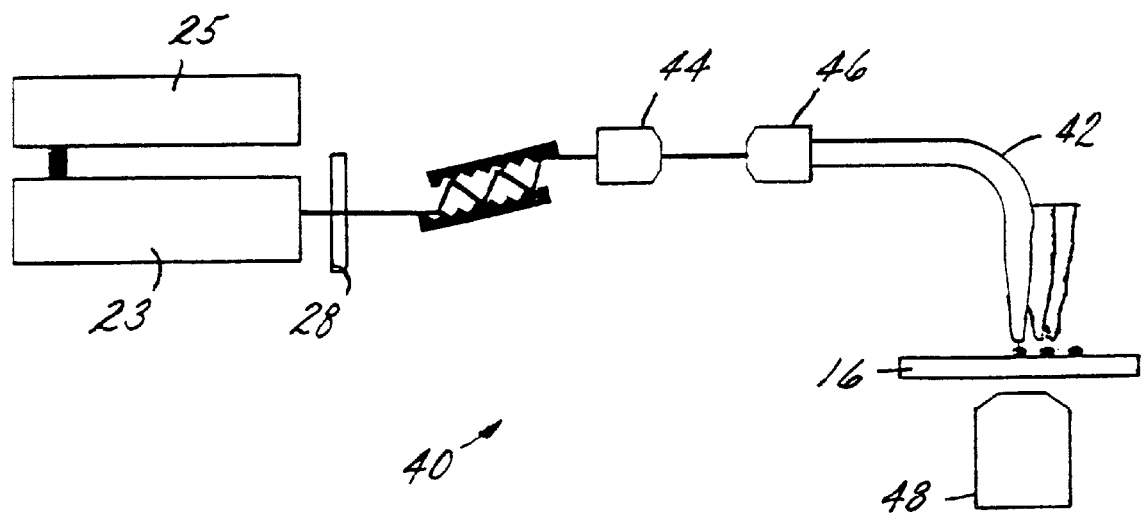
FIG. 4 is a schematic diagram of an apparatus having near field optics suitable for fabrication by multi-photon excitation.

In another embodiment, use of multi-photon near field optics results in the formation of structures comprising point volumes having X,Y, and Z dimensions of less than about 50 nm. The apparatus 40 of FIG. 4 is suitable for practice of this embodiment, comprising fiber optic couplers 42, 46 in conjunction with near field fiber optic element 42. Near-field optics excitation circumvents the diffraction limited ($\lambda/2$) resolution of optical microscopy by interrogating the sample with light from a small aperture at a separation much shorter than the excitation wavelength. The limiting aspect of scanning near-field optical microscopy (SNOM) is the photon flux through the fiber-optic aperture. Typically, probes are coated with aluminum to confine the light to the near field. However, these probes become damaged at power levels above a few nanowatts of continuous wave excitation. Uncoated probes can transmit much higher laser power, and if used in an epi-illumination geometry can still provide resolution below the optical diffraction limit. SNOM has also been demonstrated using continuous wave two-photon excitation through uncoated probes on fixed samples. This showed better axial confinement than possible with one proton excitation (OPE). For near-field fabrication, two-photon excitation is employed, using, for example, uncoated cantilevered fiber probes 42. Optional optical microscope 48 may be present as an imaging element. The method is effective, for example, in writing suboptical features (50–100 nm) onto larger objects produced via either laser or stage scanning. This technique finds particular application in controlling biological processes such as statistically localizing single proteins or enzyme molecules.

In another embodiment, the optical element of the near-field embodiment is coupled with a multiple-barrel pipette (shown in shadow in FIG. 4) for extremely precise delivery of specific components into identified areas. Light delivery may occur through one barrel of the multiple-barrel pipette by coating the inside of the light-delivering pipette with an opaque material, or conversely, by coating the inside of the reagent-delivering pipettes with an opaque material. Micropipetting of very small amounts of material is known in the art, including but not being limited to syringe pumps, ultramicrosyringe pumps, or iontophoretic methods. A bundled micropipette is used to deliver multiple agents simultaneously or sequentially, or is used for a sequence of rinsing one or more times, delivering active agent(s), and rinsing again one or more times. Alternatively, finer delivery (smaller amounts) may be achieved with iontophoretic methods. Amounts of agents delivered may be varied by varying the size of the micropipette, or the delivery time.

A variety of precursor materials are suitable for use in the present method, as long as such compositions do not substantially absorb the radiation used for polymerization or crosslinking adjacent to the focal point. Substantial transparency allows more precise focus of the laser beam, and minimization of unwanted side reactions. Use of visible, near infrared, infrared, or deep red illumination also minimizes damage to precursors adjacent to the focal point since most organicl inorganics, polymers, proteins, nucleic acids, and lipids have minimal absorbance and scattering cross-sections at red and near-IR wavelengths. Reaction of the precursor solution in accordance with the present invention may occur in bulk (in either liquid or solid phase), in solution, adsorbed to a substrate, or in suspension or emulsion. Any solvent must also be substantially transparent to the radiation used to fabricate the structures.

One type of suitable precursor compositions are polymerizable or crosslinkable (usually by free radical or cationic mechanisms) upon photoinitiation. Photoinitiable polymerizable or crosslinkable precursor compositions will therefore ordinarily comprise an initiator for initiation of the reaction, as well as monomers, oligomers and/or polymers and/or crosslinkers capable of free radical or cationic chain propagation and chain termination steps. The initiator may or may not be covalently attached to the crosslinker, monomer, oligomer, and/or polymer. la Suitable photoinitiators for radical polymerization include, but are not limited to azo compounds such as azobisisobutyronitrile, peroxides such as benzoyl peroxide, aliphatic carbonyl compounds such as ketones and diketones, and aromatic diketones such as benzophenone and its derivatives, and 9-fluorenone 2-carboxylic acid. Other photoinitiation systems include, but are not limited to, redox-type photoinitiators useful in aqueous systems (e.g., ion pairs such as $Fe^{3+}OH^-$, and $Pb^{2+}Cl^-$), photosensitive dyes such as eosin, rose Bengal, and erythrosin, and transition metal derivatives such as $Mn_2(CO)_{10}$ in the presence of organic halides.

Suitable free radical polymerizable compounds include, but are not limited to cross-linkers, monomers, oligomers and/or polymers having at least one olefinic (unsaturated) bond, such as crosslinkers, monomers, oligomers and/or polymers which form polyalkylenes and halogenated polyalkylenes, polyacrylates, polymethacrylates, polyacrylamides, and styrenes.

Photoinitiators for cationic polymerization include but are not limited to triarylsulfonium and diaryliodonium salts with complex metal halide anions, and mixed arene cyclopentadienyl metal salts of complex metal halide anions, such as (6-benzene)(5-cyclopentadienyl)Fe(II) hexafluorophosphate. Suitable cationic polymerizable compounds include but are not limited to epoxides such as cyclohexene oxide.

Photopolymerizable precursor compositions are also suitable for use with the present invention. In photopolymerizable compositions each propagation step is effected by the incident radiation, and photopolymerization may be achieved using photo-crosslinking agents such as bisarylazides or photocross-linkable oligomers and polymers. Such oligomers and polymers contain chromophoric groups that undergo light-induced chemical bonding with each other. The chromophoric groups may be in the polymer backbone, for example a backbone chalcone group, or pendent, for example a poly(vinyl cinnamate).

The above descriptions of suitable precursors are categorized by reaction mechanism for the purposes of convenience only. It is to be recognized that other polymerizable or crosslinkable precursors, alone or in combination with other photoinitiators, are also within the scope of the present invention, wherein the precise mechanism of polymerization (e.g., radical polymerization, single electron polymerization, or photopolymerization) is not clearly known. Thus, essentially any precursor composition which is photo-activated to form cross-links with the fabricated construct with or without an intermediary cross-linker, and which is substantially transparent to the radiation outside the focal point is within the scope of the present invention. Such precursors include, but are not limited to, the above-described and other organic monomers (including dyes and chiral species), oligomers, and polymers, including biopolymers.

Biological monomers and polymers are of particular interest, including but not being lmied to amino acids, peptides and proteins; fatty acids and lipids; nucleotide, oligonucleotides, and their synthetic analogues; nucleic acids; sugars and carbohydrates; bioactive agents such as cytokines, hormones, receptors, growth factors, and drugs; optically active synthetic agents (including inorganic compounds); and optically active bio-compounds such as caged compounds and fluorophores. These molecules are not readily amenable to nanofabrication, as they are often only sensitive to UV light, and must be reacted in solution, problems which are solved by the present method.

Figure 5:
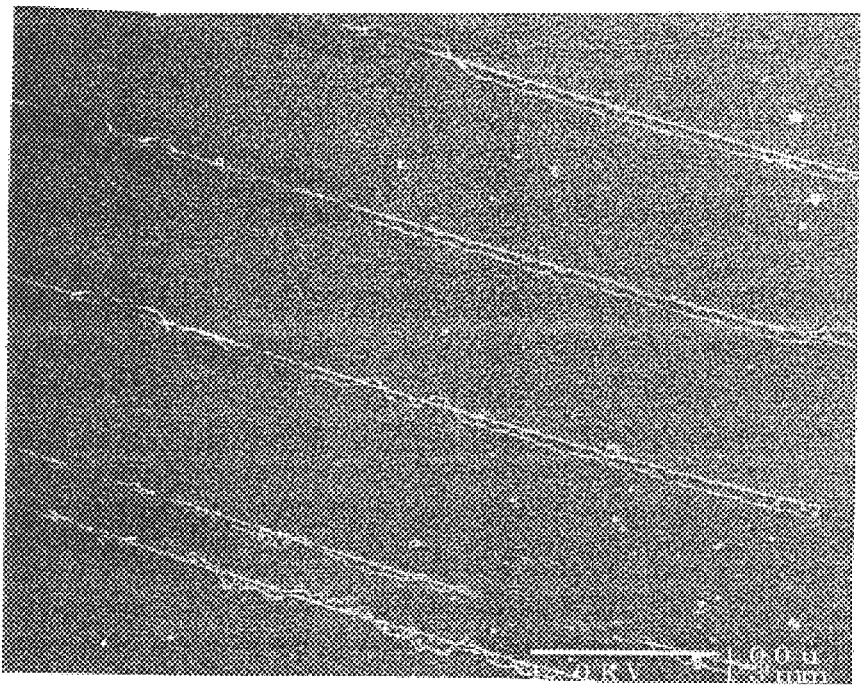
FIG. 5 is a scanning electron microscope (SEM) image of multiple polyurethane rods fabricated by two-photon excitation.
Figure 6:
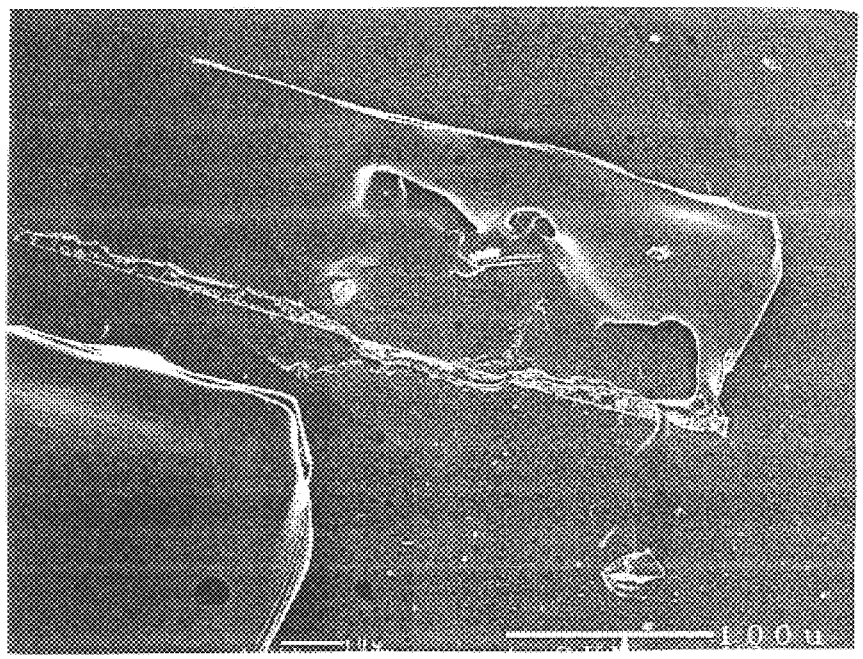
FIG. 6 is a scanning electron microscopic image of a polyurethane sheet manufactured in accordance with the present invention.
Figure 7A:
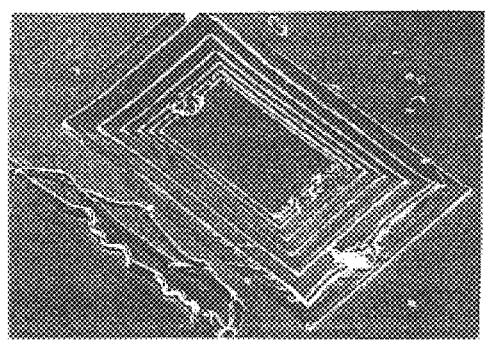
FIGS. 7A and 7B are SEM images at low (7A) and high (7B) magnifications showing the successive lamellae of a pyramidal structure fabricated using two-photon excitation of a polyurethane precursor.
Figure 7B:
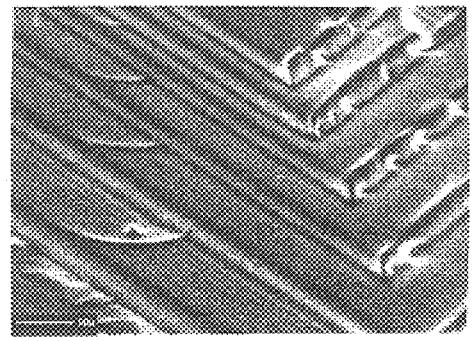

As described in the Examples below, a number of organic polymers in various configurations have been fabricated. Polyurethane structures have been assembled and cross-linked using an optical adhesive preparation commercially available from Norland under the trade name Optical Adhesive #83H (FIGS. 5, 6, and 7A–B). FIG. 5 is an SEM image of multiple polyurethane rods formed by two-photon induced polymerization of a polyurethane precursor solution as described in Example 1. FIG. 6 is a scanning electron micrograph of a polyurethane sheet fabricated by two-photon excitation. Based on observations using transmitted light microscopy immediately after fabrication, the sheet was unitary upon fabrication. The irregularities observed in the SEM are thus artifacts caused by rinsing and air drying in preparation for SEM imaging. Finally, FIGS. 7A and 7B are SEM images at low (7A) and high (7B) magnifications showing the successive lamellae of a pyramidal structure fabricated using two-photon excitation of a polyurethane precursor.

Figure 8:
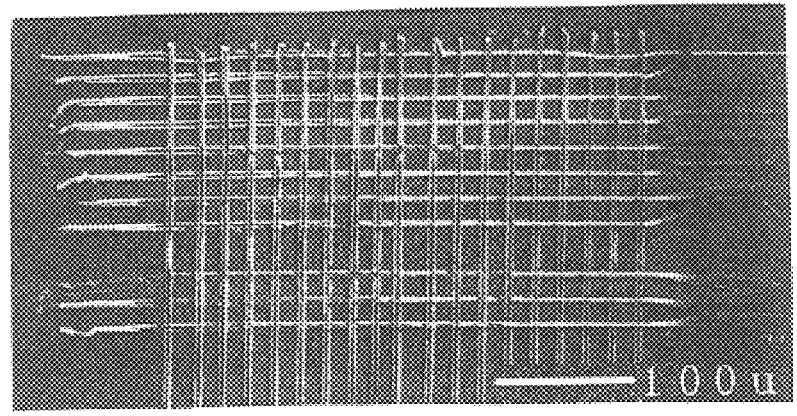
FIG. 8 is an SEM image of a lattice structure fabricated by three-photon activation of trimethylol triacrylate.
Figure 9:
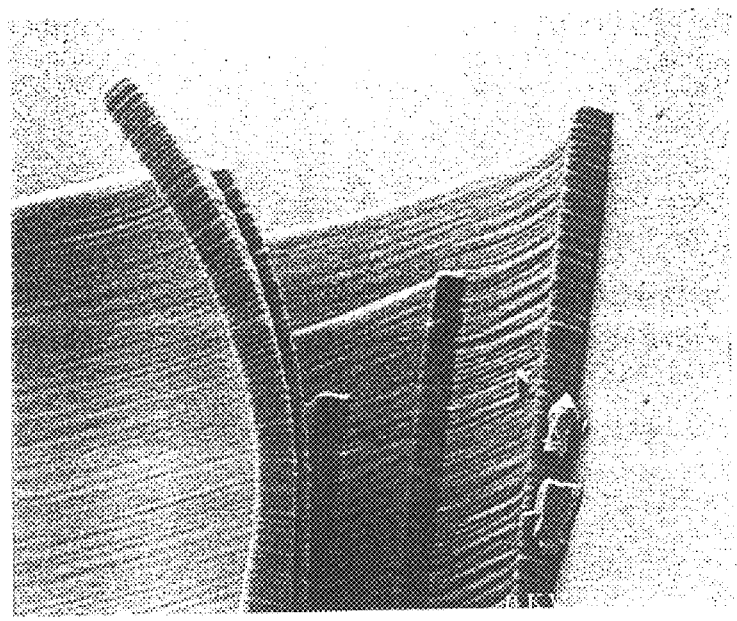
FIG. 9 is an SEM image of stacked layers of polymerized trimethylol triacrylate sheets fabricated by multi-photon excitation.

Trimethylolpropane triacrylate has been polymerized in combination with Rose Bengal (two-photon excitation) or 9-fluorenone-2-carboxylic acid (three-photon excitation). FIG. 8 is a scanning electron microscope (SEM) image of a lattice formed by rods of trimethylol triacrylate polymerized by three-photon activation in the presence of 9-fluorenone-2-carboxylic acid and triethanolamine. FIG. 9 is a scanning electron microscope (SEM) image of stacked layers of polymerized trimethylol triacrylate sheets fabricated by multi-photon excitation. The top layers in the image were peeled back during preparation for SEM to reveal the inner, layered structure. Fabrication was initiated by 3-photon activation of 9-fluorenone-2-carboxylic acid in the presence of triethanolomine.

Figure 10:
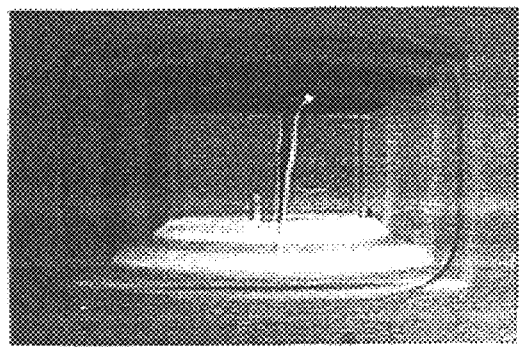
FIG. 10 is transmitted light micrograph showing a pyramid fabricated from three layers of 40% polyacrylamide.

Polymerization of acrylamide using two-photon excitation in the presence of several other activators has been used to fabricate three-dimensional structures as in FIG. 10, which shows a pyramid fabricated from three layers of 40% polyacrylamide.

Figure 11:
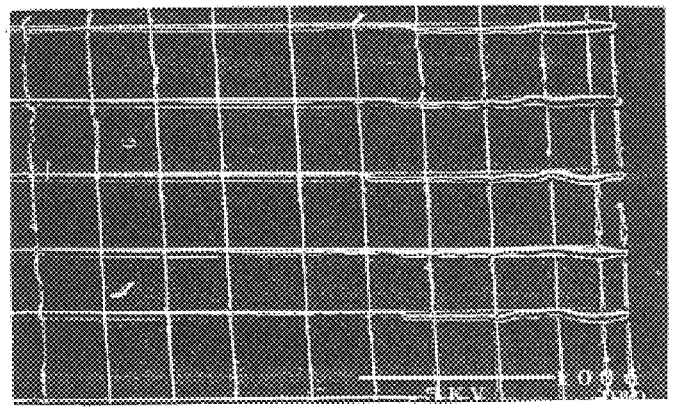
FIG. 11 is an SEM image of a composite lattice comprising polymerized bovine serum albumin (vertical lines) and polyurethane (horizontal lines).
Figure 12:
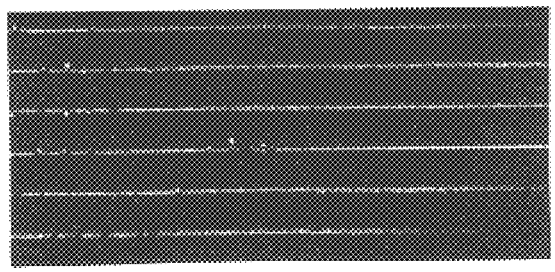
FIG. 12 is a fluorescence micrograph showing several rods of BSA labeled with Texas red, fabricated by two-photon excitation from an aqueous solution of BSA.
Figure 13:
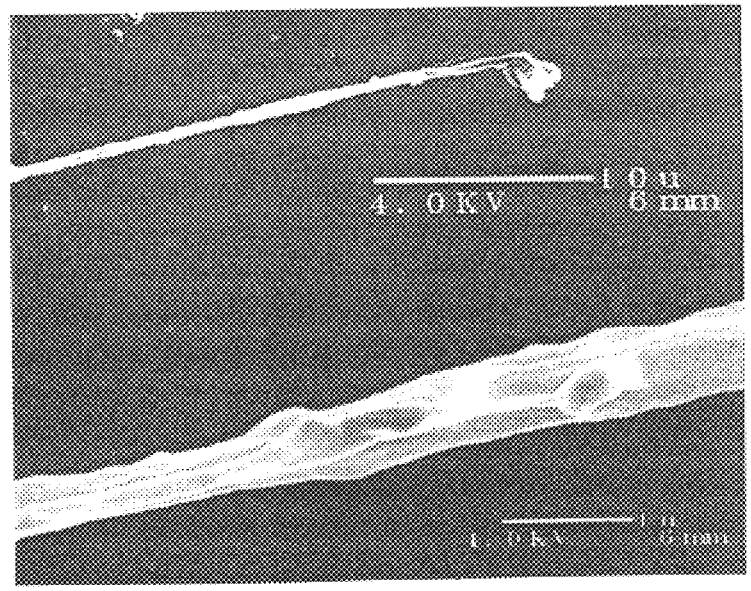
FIG. 13A and 13B are SEM images of a rod fabricated from BSA using three photon excitation at (A) lower and (B) higher magnifications
Figure 14:
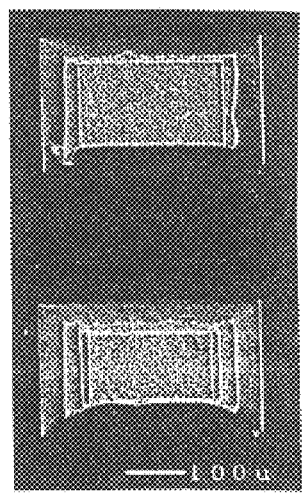
FIG. 14 is an SEM image of pyramids fabricated from polymerized BSA.

Fabrication has also been demonstrated with biologically active molecules. Bovine serum albumin (BSA, a soluble globular plasma protein) in an aqueous solution has been is polymerized into a synthetic construct in the presence of Rose Bengal (FIGS. 11, 12, and 14) and in the presence of the photoinitiator 9-fluorenone-2-carboxylic acid and triethanolamine (FIG. 13). FIG. 11 is an SEM image of a composite lattice comprising polymerized bovine serum albumin (vertical lines) and polyurethane (horizontal lines). FIG. 12 is a fluorescence micrograph showing several rods of BSA labeled with Texas red (Molecular Probes). The rods were fabricated by two-photon excitation from an aqueous solution of BSA using Rose Bengal as an activator. FIGS. 13A (lower magnification) and 13B (higher magnification) are SEM images of a rod formed by three-photon excitation in the presence of 9-fluorenone-2-carboxylic acid and triethanolamine. FIG. 14 shows SEM images of pyramids fabricated from polymerized BSA using two-photon activation in the presence of Rose Bengal.

A number of factors affect the ultimate dimensions and degree of polymerization or crosslining of the formed construct, and thus the ultimate properties and dimensions of the final structure. Such factors are often interrelated, and include, for example, the size of the focal point, the identity of the precursors, the mechanism of crosslinking or polymer formation, the substitution patterns of the reactive groups, the stability of intermediates, diffusion of intermediates or precursors, the competing reactions, the presence of reaction accelerators or inhibitors, and the like. For example, without being bound by theory, it is hypothesized that smaller structural dimensions are obtainable by the method of the present invention when less stable reactive intermediates are generated, or when the number of chain propagation reactions is limited. Larger structures may be synthesized using more stable intermediates, thereby allowing one or a combination of radical species to diffuse away from the focal point of the laser, or for chain polymerization to occur beyond the focal point of the laser, and terminating only upon the occurrence of chain terminating steps. Smaller species may also diffuse beyond the focal point of the laser, ultimately leading to larger structures. Focus of photon density partly within an inactive substrate of other inactive locale will result in a smaller construct.

In case of the polyurethane and albumin, however, free radical (or single electron) polymerization or cross-lieing may occur, but only to a limited extent because of the instability of the formed free radicals or the favored energetics of chain termination steps. Alternatively, photopolymerization alone may occur, which by its nature is limited to the focal point of the laser. In any event, the size of the formed structure depends not only on the size of the laser focal point, but also on the nature of the precursor composition, wherein less-stable radicals or other intermediates result in structures having smaller dimensions.

A significant advantage of the method of the present invention is that it allows fabrication of micro- and nano-sized structures having almost unlimited geometries. As mentioned above, two- or three-dimensional objects are formed by successive movement of the laser beam and/or the stage containing the reactive species until the desired structure is built point by point. The morphology of the final structure will thus depend at least in part on positional control of the beam or the stage used for polymerization.

Objects comprising multiple materials may also be fabricated, by changing the precursors sequentially. Alternatively, precursors with different wavelength sensitivity may be used in conjunction with a variable wavelength laser or multiple lasers. Changing the wavelength allows selective fabrication of two or more components at the same time (this process is illustrated schematically in FIG. 1). The fabrication method of the present invention may also be used in conjunction with other fabrication methods, such as physical trapping of a compound within an optically nano-fabricated cage, gel, or matrix.

In one embodiment, multi-photon free-form fabrication is used to place active (preferably bioactive) into three-dimensional photo-crosslinked and/or photo-polymerized gels or constructs which have controlled release, controlled degradation, and/or controlled diffuisivity properties. Bioactive agents which may be so placed include, but are not limited to growth factors, nucleotides (DNA, RNA, antisense), ions, buffering agents, dyes, proteins, peptides, carbohydrates, glycosaminoglycans, enzymes, nucleotides, liposomes, cells, and and drugs. Diffusion of the agent or agents out of the construct is adjusted to effect controlled release, or to expose or otherwise bring the entrapped agent or agents to the construct surface or other interface to enable bioactivity. Diffusion is controlled by one or a combination of methods, for example by control of the affinity of the agent or agents for the construct, control of the degree of crosslink density of the construct, or control of the rate of degradation of the construct. Control of the degree of affinity of the agent or agents for the construct may be achieved by appropriate selection of the construct composition, e.g, backbone and/or crosslink compositions. Use of differing cross-linking moieties allows adjustment of relative affinities of two or more agents. Entrapment of agents having different construct affinities allows controlled release at different rates.

Control of diffusion and degradation properties is most readily achieved in a chemically uniform gel by locally varying the crosslink or polymerization density. This may be achieved by varying illumination time, intensity (photon energy density), and/or by altering gel architecture, including variation of the gel's spatial dimensions, addition of overlayers of gels without entrapped reagents, and other three-dimensional patterning. Control of diffusion and degradation can also be achieved by varying gel chemistry, such as by varying cross-link chemistry, using different monomers, and by altering the rate of polymerization or cross-linking by changing other reactant constituents.

In another embodiment, multi-photon free-form fabrication is used to place active (preferably bioactive) agents into three-dimensional photo-crosslinked and/or photo-polymerized gels or constructs more permanently. Alkaline phosphatase has been entrapped in polyacrylaride gels as described in Example 7. Higher density gels inhibit diffusion of a reagent into gel from the edges. Enzyme activity is also decreased in regions where the construct is in closer contact with the substrate. It is theorized that diffusion of reagent is inhibited in these regions.

In one form of this embodiment, such entrapped agents include entrapped enzymes that continuously act on molecules which diffuse into the gel or construct before the molecules diffuse out of the gel or construct. In another form, such entrapped agents include entrapped enzymes, chelators, or other molecules which act on molecules which diffuse into the gel, and through this action become unable to leave the gel or construct. Entrapped agents provide a filtration or trapping function, which may be useful in biosensor and other detection applications. In another form of the present embodiment, such entrapped agents include entrapped motile proteins, peptides, or non-biochemical structures which cause the fabricated construct to wiggle, change shape, or change its diffusion properties when specific molecules, ions, or others agents difuse into the gel. In another form of the present embodiment, such entrapped agents include entrapped photodynaric molecules which change color, refraction, diffusion, transport, shape, or other physical properties or biochemical activities when illuminated at certain wavelengths, polarizations, or other states of light. In another form of the present embodiment, such entrapped agents include entrapped chemoactive molecules which change color, refraction, diffusion, transport or other physical and/or biochemical properties due to the activity of chemical agents which diffuse into a gel or other construct such as ions, pH, and biomolecules.

Manufacture of gels comprising entrapped proteins is particularly useful for fabrication of detection and separation systems which function on nanometers to micron scales. An example of this type of fabricated gel includes entrapment of proteins selected from the group consisting of nano-Ochterlony-like immunodiffusion assays (for antigen- antibody precipitation), nanoscale polyacrylamide electrophoresis (PAGE) gels, PAGE gels with optically fabricated nanoscale gradient densities, and nanoscale separations and detection systems such as Southern blot, Western blot, Northern blot, and polymerase chain reaction (PCR) wells.

Entrapment (or encapsulation) of living cells in particular has application in tissue engineering, cell culture, cell bioreactors and in detection (biosensor) systems. Such entrapment may be temporary or permanent. It is known that multi-photon microscopy generally has minimal effect on cell viability, due to the long wavelengths used and the highly spatially restricted excitation zone. The optical aspect of fabrication is thus unlikely to provide any major impediments to cell entrapment.

Entrapment includes both physical entrapment of cells within a construct, such as a gel or a scaffold, chemical cross-llnning of the cell surface to a construct, or crosslinking of one cell to another. Encapsulation of cells is by polymerization of the construct around the cell. Where necessary, the potential for any photodamage is minimized by building a "box" around a cell without directly contacting the cell so entrapped. Since the optical zone for fabrication is limited to a few hundred nanometers, which is much smaller than a cell, photo-excitation may be limited to specific cell regions. The present method thus also includes directly cross-inking or "tethering" cells to constructs by directly linking the construct to, e.g., cell-surface glycoproteins. This effectively provides a means to establish cell positioning on a scaffold. Preferred cells for this application is cells having robust cell walls, such as bacteria and plant cells. Multi-photon excitation may also be used to provide cross-linking within and between cells which have been entrapped.

Figure 15A:
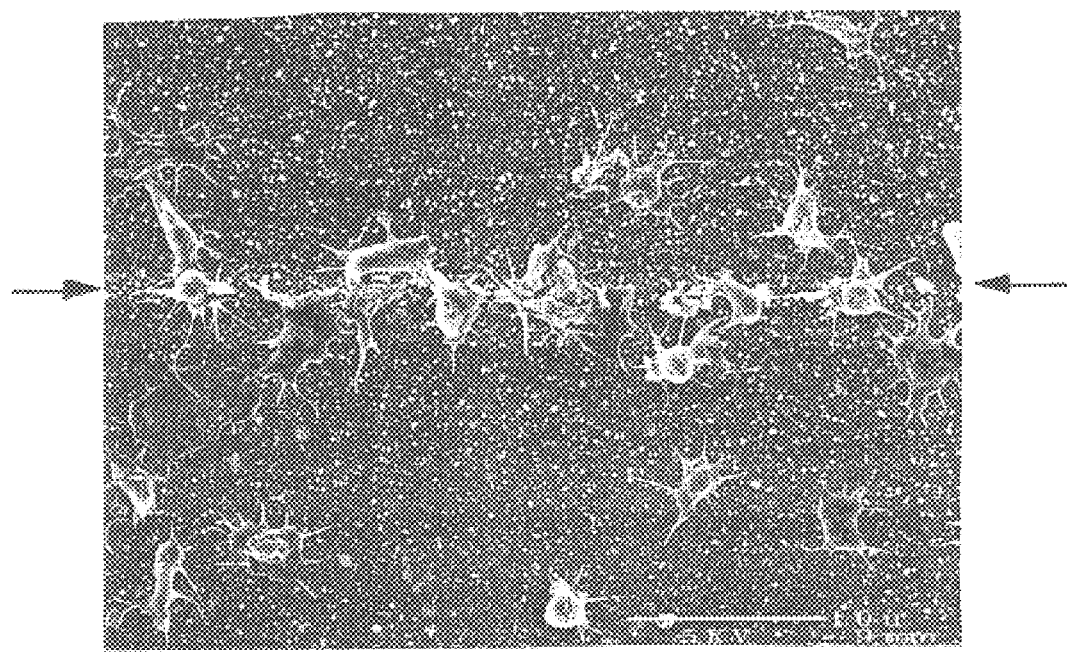
FIGS. 15A and 15B are SEM images of human blood platelets (A) adhered to a line comprising crosslinked fibrinogen, which is on top of a crosslinked region of bsa; and (B) a nonfabricated region of glass substrate, which was exposed to BSA and fibrinogen fabrication solutions but where optically-induced fabrication occurred.
Figure 15B:
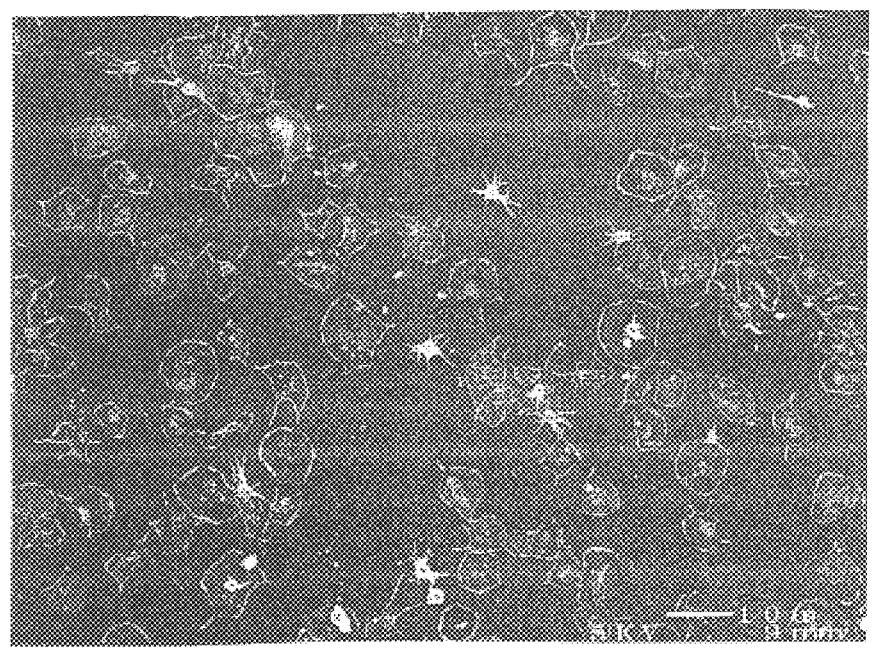

In another embodiment, multi-photon excitation is used to modify the surface of materials which have complex textures, chemistries, or biochemistries, or to provide complex textures, chemistries, or biochernistries to surfaces. Exemplary surface modification includes the attachment of active agents directly to cell surfaces by multi-photon mediated cross-linking. This would facilitate delivery of agents directly to specific cells, complemented by pinocytotic processes, which cause these agents to be taken into the cell. Another example is addition of one or more bioactive finctions or detection elements to a substrate such as in integrated circuit or other device. The fine positioning of such functions or elements using the microscope portion of the apparatus represents an important advantage of the present technology. An example of such surface modification is the fabrication of fibrinogen scaffolds for the adhesion of blood platelets. FIG. 15A shows an SEM image of human blood platelets adhered to a line comprising crosslinked fibrinogen, which is itself fabricated on top of a rectangular region of fabricated albumin. Almost all of the platelets are adherent to the fibrinogen feature, or to other platelets which are adherent to the fibrinogen. Platelets adherent to the BSA background exhibit minimal spreading. FIG. 15B in contrast, which has no BSA or fibrinogen constructs, exhibits a random adhesion pattern, and extensive platelet spreading.

An especially useful application employing surface modification is the manufacture of biomimetic surfaces for use with tissue cell culture, especially the provision of surfaces which replicate biological textures such as subendothelial and subepithelial extracellular matrices and basement membranes, and other tissue topographies. U.S. Pat. Nos. 5,380,589 and 5,700,241 are relevant in this regard. The surfaces of bone implants may be modified as described in U.S. Pat. No. 5,370,692 to Fink et al., which is incorporated by reference herein.

Another example of surface modification using multi-photon excitation is the manufacture of micromachines using motile proteins, for example by affixing kinesin, microtubules, actin, axonemes, flagella, or other motile structures to fabricated constructs in a spatially organized manner. This is used to manufacture ciliated surfaces or devices to transport molecules along a desired path or to make devices which move using biochemically driven mechanisms.

Figure 16:
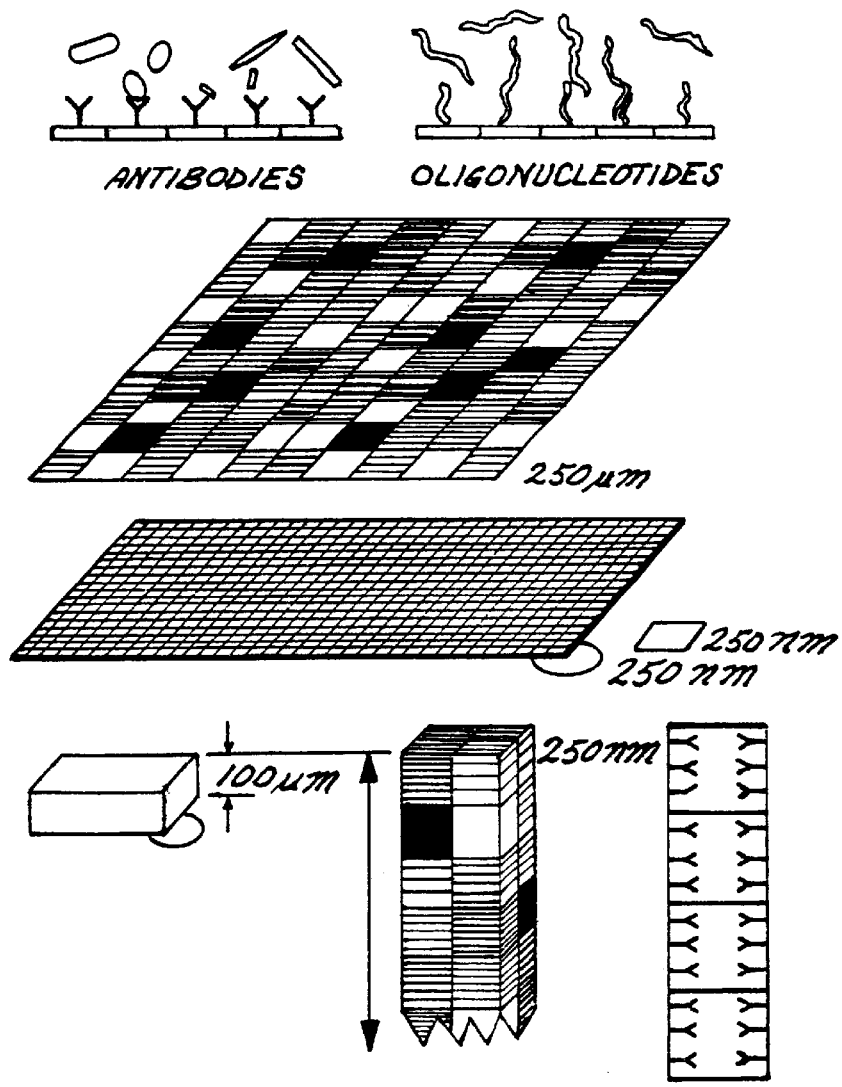
FIG. 16 is a schematic diagram of a biosensor array chip.

In another embodiment, multi-photon fabrication is used to manufacture biosensors, environmental sensors, and chemical sensors. A schematic diagram of a biosensor array chip using, for example, antibodies or oligonucleotide is shown in FIG. 16. Current technology can achieve about $1.5 \times 10^3$ assay sites per square centimeter. The nanofabrication technology of the present invention could conservatively achieve a density of $1.6 \times 10^9$ assay sites/cm$^2$ in two dimensions using multi-photon exdtation, or conservatively up to $6.4 \times 10^{11}$ assay sites/cm$^2$ in three dimensions using multi-photon excitation. U.S. Pat. No. 5,556,752 to Lockhart et al., which is incorporated by reference herein, discloses an array of double-stranded oligonucleotides on a solid support usefl for screening.

In another embodiment, the present method is used to provide spatial orientation of enzymes, antibodies, receptors, ribosomes and the like relative to substrates or within manufactured constructs in order to produce useful biochemical or chemical work from such assemblies. These "biochemical factories" may be biomimetic in overall organization or artificial, in the sense that novel structures are produced. Such factories include arrays of enzymes to effect electron transfer, to perform biochemical synthesis, to perform separations, and to cause biomolecules in solution to interact with those in the fabricated device with specific orientations.

Fabrication with the appropriate spatial and biochemical organization allows several enzymes to act, in turn, on added reactants for synthetic, degradative, transport, transduction, and/or other functions. To effect proper orientation of enzymes and the like during fabrication, external forces may be applied such as electrostatic an/or magnetic fields, shear forces, laser tweezers, and magnetic tweezers. Proper orientation may also be facilitated by permitting self-assembly by using other molecules as chaperones, and by using flexible tethers to connect enzymes and the like to substrates. Another method is to bind soluble macromolecules to link structures together in solution, and then to link the entire unit to the device to be fabricated where desired, followed by macromolecular ligand release. Macromolecular ligand release may be mediated by altering ionic strength, use of soluble enzymes, or other processes, thereby leaving the desired molecule on the surface in the proper orientation to bind ligands.

In another embodiment, multi-photon excitation is used to modify explanted tissue prior to re-implantation. In in vitro tissue modification, the tissue is first removed, through for example, a homograft, allograft or xenograft. The properties of the removed tissue are then modified by effecting cross-lking by multi-photon excitation with suitable crosslinking agents, and/or by diffusing in agents to incorporate specific activities or to effect other processing. The tissue is then implanted or otherwise used. A specific example of this methodology is the improvement of physical properties and decrease in potential infection and calcification of tissue-based xenogeneic heart valves. Increases in strength, alterations in flexibility, or improvement of other properties such as decreasing or eliminating the need for aldehyde and other chemical cross-linking fixations is achieved by selectively incorporating crosslinks into identified regions using multi-photon excitation. Incorporation of agents (e.g., chelating agents or antibacterial agents) into the xenogeneic tissue by crosslinking will result in decreased calcification and susceptibility to infection, respectively.

In another embodiment, multi-photon excitation is used to fabricate molds, stampers, masks, or other forms for multiple production. In particular, masks for photolithography having smaller dimensions than those presently in commercial use are available by the present method. Currently, high-resolution masks for research purposes with features in the range of about 150 nm are very expensive. The present technology allows fast, efficient production of such masks with comparably-sized or smaller features, and with multiple precursor types. Another application of this type is surface molds for biomimetic extracellular matrix textured surfaces for tissue culture, tissue engineering, and biomaterials.

Figure 17:
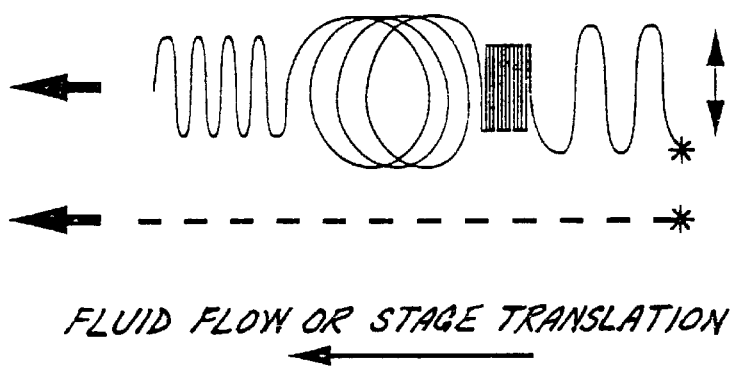
FIG. 17 is a schematic diagram illustrating the wide range of topologies achievable using galvo scanning and galvo-scanning motion in the X-Y directions for (A) continuous fiber output and (B) pulsed fiber output (via, e.g., beam shuttering ) within the solution.
Figure 18:
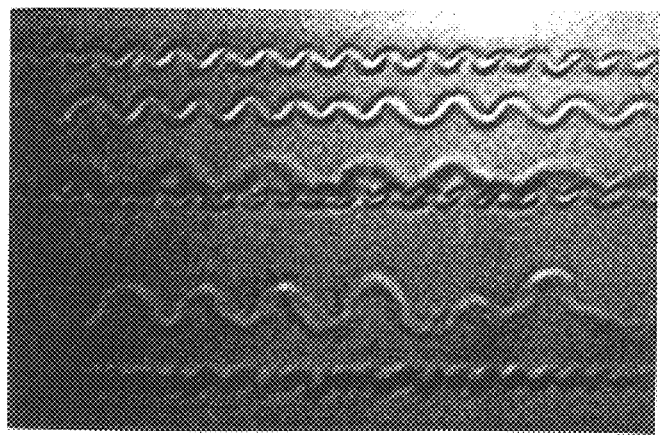
FIG. 18 is a transmitted light microscope image of a series of helices having a line thickness of approximately 350 nm formed by two-photon fabrication of polyacrylamide.

FIG. 17 illustrates the wide range of topologies achievable using galvo scanning and galvo-scanning motion in the X-Y directions for (A) continuous fiber output and (B) pulsed fiber output (via, e.g., beam shuttering). In another embodiment, fabrication by multi-photon excitation is used to control shrinkage or expansion effects upon polymerization of the exemplary structures shown in FIG. 17 (as well as other structures), and may be used to create more complex three-dimensional structures from simpler two-dimensional precursors. Structural complexity may be achieved by varying gel/polymer density by altering illumination intensity, chemistry, scan time, scan pattern. For example, FIG. 18 shows a transmitted light microscope image of a series of helices having a line thickness of approximately 350 nm formed by two-photon fabrication of polyacrylamide. Fabrication was by scanning in a straight line through a bulk monomer solution. The decrease in acrylamide volume upon polymerization induced the lines to twist into helices. The spatial frequency was altered by optically inducing different cross-link densities by varying dwell time, and by physically constraining the helix by partial contact with the substrate. The "double helix" (third from the top in FIG. 18) arose from an attempt to place one helix inside another.

In another embodiment, dynamic shape change in formed objects is achieved by using Poisson ratio effects, controlled shrinkage/expansion effects, and/or by incorporating chemical groups, proteins and other elements into the precursor compositions which, upon polymerization or crosslinking will swell or otherwise change shape. Such elements optionally include a "smart" polymer or a biopolymer, such as an enzyme or motile protein, which will change its shape (for example, bend, elongate, shrink, move, or coil) with a change in media condition (for example, temperature, solvent, ionic strength, or addition of specific ligand). Such materials may be used as actuators, i.e., to dynamically change shape to exert physical force, alter fluid flow, or change other properties. As examples of the present method, biosynthetic mechanical structures may be produced by placing tubulin monomers at ends of a nanofabricated rod to make a dynamic cytoskeletal-like element; a kinetochore may be incorporated to form microtubules; or profilin may be incorporated to form actin. Additionally, change in the shape of a structure may be used to open or close pores (i.e., act as a variable filter), or to expose an active finctionality such a one or more antibodies or cell surface receptor ligands. Such structures would as a second functional element to "trap" antigens or specific cells.

Figure 19:
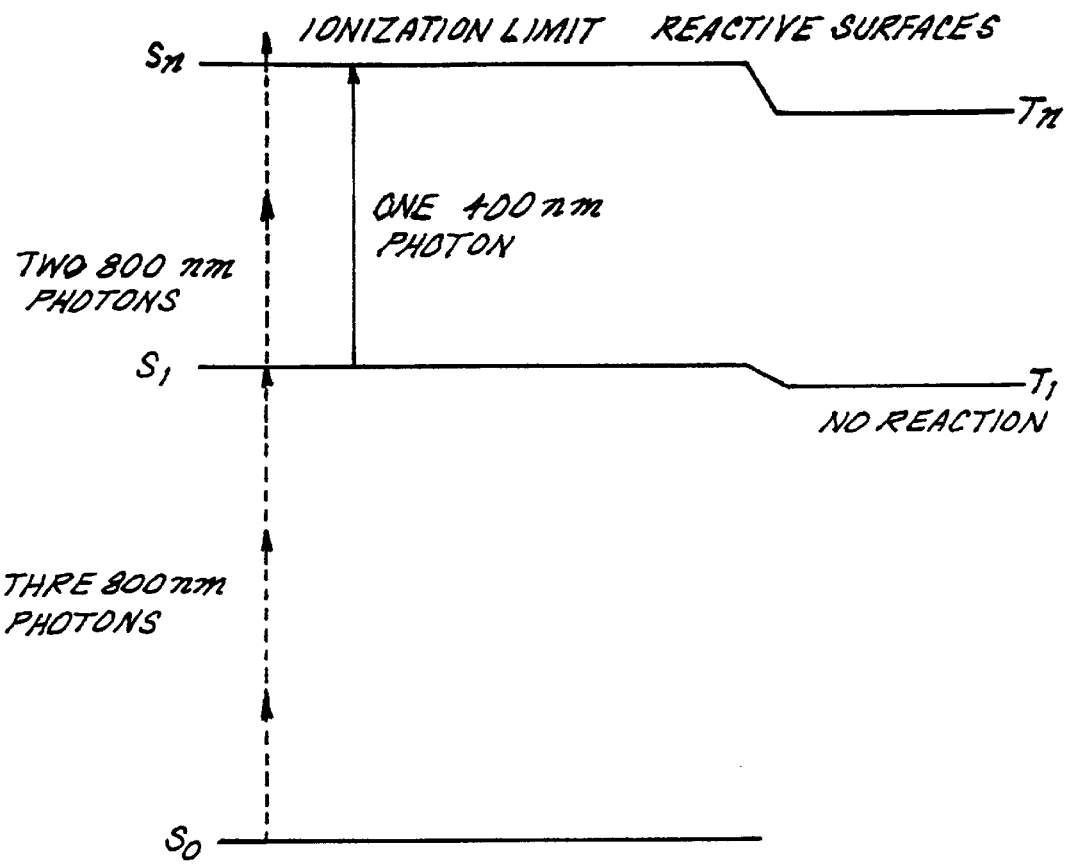
FIG. 19 is a schematic diagram illustrating direct protein crosslinking by multiphoton excitation without the addition of photosensitzers or chemical crosslinkers.

In another embodiment, multi-photon excitation is used for direct protein crosslinking without the addition of photosensitzers or chemical crosslinkers, as illustrated in FIG. 19. The $\pi$ to $\pi^*$ transition (266 nm) of proteins or peptides containing aromatic residues is excited by simultaneous absorption of three 800 nm photon of 100 femtosecond pulse width. Following this excitation a second time delayed beam excites the chromophore above the ionization limit. This is done by a two photon process with 800 nm or by one photon of 400 nm. Transiently, the chromophore forms a zwitterion which covalently binds to a second protein or peptide. The power dependence of the multi-photon absorption process leads to three-dimensional confinement of activation on the microscopic scale. Such confinement is defined by the initial three photon process and the second step may therefore proceed equivalently with one or two photon excitation.

The method of the present invention is further used to manufacture optical devices in layers and in other two and three-dimensional configurations, using chiral and optically-active compounds having specific organizations. By virtue of assembly of elements smaller than most visible optical wavelengths, such assemblies are effective to alter diffraction, refraction, become optical waveguides, and otherwise manipulate optical properties.

Figure 20A:
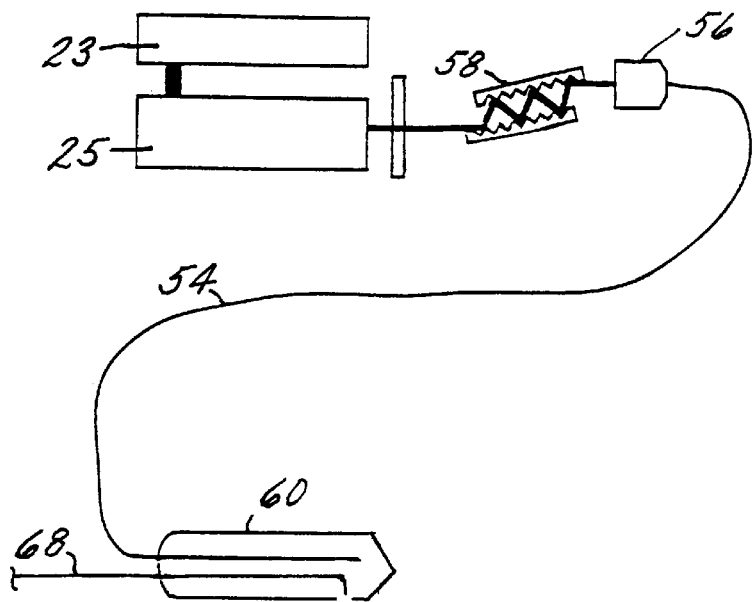
FIGS. 20A–C are schematic diagrams illustrating an apparatus suitable for fabrication by multiphoton excitation at remote locations.
Figure 20B:
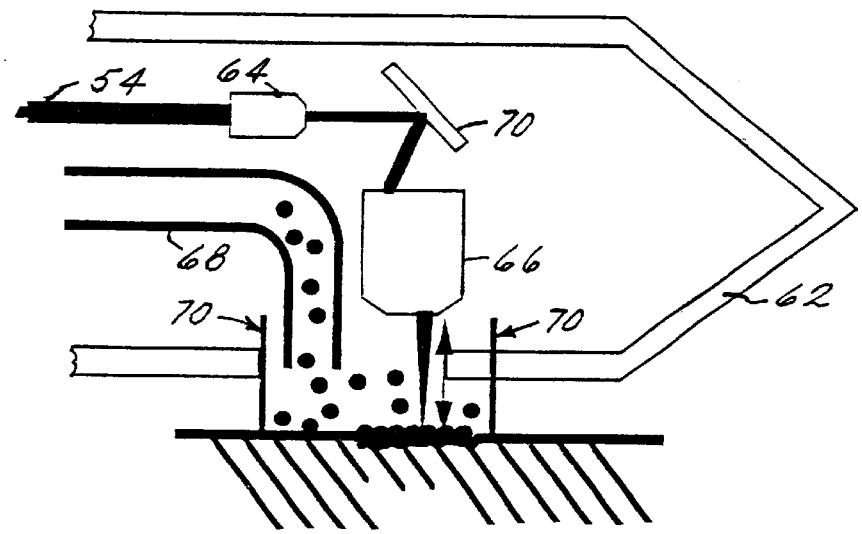

In another embodiment, at least one fiber optic element is used to effect nanofabrication by multi-photon excitation in locations which are otherwise inaccessible, preferably by using a fabrication apparatus in combination with a catheter. As shown schematically in FIG. 20A, a photon source, preferably a an argon ion pulse laser 23 in combination with a Ti:Sapphire laser 25, sends red or infrared light into a single mode optical fiber 54 via a fiber optic coupler 56. A group velocity delay self-phase modulation (GVD/SPM) compensator 58 is used to compensate for optical dispersion and to minimize spectral broadening within the fiber. The optical fiber is placed inside a flexible tube to provide support and protection. For medical application this tube may be a catheter 60 to permit access to internal organs. FIG. 20B is a detail in section of catheter 60, comprising catheter housing 62 for optical fiber 54 and reagent tube 68. The single mode fiber 54 is then coupled via fiber optic coupler 64 to lens 66 which provides focusing to the fine point necessary for multi-photon fabrication processes. The lens 66 may be of any numerical aperture (NA) in the range of 0.1 NA to as high as 1.2 NA for aqueous immersion applications, such as encountered in vivo, in order to effect the region size and photon density for multi-photon activation.

Several mechanisms may be used to effect the placement of the lens at the focal distance from the point where fabrication is desired. A cowling 70 may be used to provide this spacing. Alternatively, spacing may be obtained by incorporating imaging capability through the catheter and providing opto-mechanical means to move the assembly, to adjust the focal length, and/or to scan a beam. Reagents for assembly and fabrication may be introduced via reagent tubes 68 tubes within the catheter. With several such reagent tubes, multiple compounds may be delivered to permit fabrication of multi-component constructs, and to provide different functionalities in different locations. In addition to fabrication, multiphoton processes can also be used for ablation, such as may be desired to clean surfaces, or as a preparative procedure prior to applying other reagents. Such catheter or fiber optic systems are of use in minimally invasive vascular and other surgical procedures, dentistry, and other applications such as for repair of pipes and conduits within man-made structures and instruments.

Figure 20C:
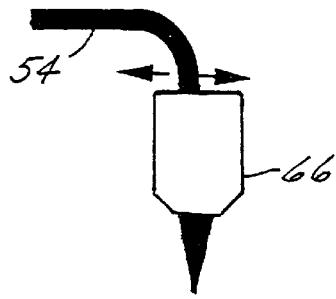

Two methods may be used for producing beam scanning with a single mode optical fiber inside a catheter. The first is use of a mirror 70 (scanning galvometer), much as is done with the non fiber-based apparatus. The second (FIG. 20C) is simpler, wherein the fiber is moved in the back focal plane of the objective lens. Single mode fibers have openings of 3 microns and coupling efficiency is approximately 50%. As described above for near-field fiber-optic probes, a post laser prism or grating pair is used to compensate for the GVD and SPM in the fiber.

Since this apparatus is basically a fiber optic microscope, this feature is exploited to image a region prior to instituting fabrication. For example, the device is used as a scanning microscope to image damaged tissue (e.g, a wound, chronic sore, corneal defect or torn articular cartilage) in situ with minimally invasive methods. Imaging may be obtained in reflective mode, as may be appropriate for teeth and other hard tissues with high reflectance, or by using multi-photon fluorescent imaging with low reflectance soft tissues. Rose Bengal, eosin, and erythrosin are exemplary nonspecific fluorescent labels, since they are diffusible, non-toxic, and also suitable pboto-initiators for fabrication. Other agents and intrinsic fluorescence may also be used.

In situ tissue repair comprises imaging a lesion in damaged tissue in three dimensions using the fiber optic device system as a scanning microscope, wherein imaging is in reflective mode (confocal) and/or in fluorescent mode using two-photon imaging, creating a three-dimensional digital map of the damage using the confocal/three-photon image(s) to calculating a plan for repair, placing repair subunits using a direct scan system, and optionally crosslinkng the edges of the repair material to the surrounding tissue to hold it tightly in place.

The multi-photon fabrication methodology, in both the in vitro and the in situ system, may be used to fabricate at some depth into tissue. Since most soft tissues exhibit considerable transmission in the near IR, tissue modification may be made to about 350 microns deep into soft tissue, such as skin and gingiva. Materials for fabrication (with low toxicity) are then diffused into tissues in the form of low molecular weight precursors. Factors for affecting effective fabrication depths are diffusion of the materials for fabrication, Rayleigh scattering of light which scales as the quartic power of the frequency, and photon density at long working distances, which is a finction of laser power and numerical aperture. Hence it is advantageous to use near infrared light to achieve significant depth.

The ability to fabricate in situ and below surfaces may be broadly applied in medicine and dentistry. Some examples include: a) delivering antisense, anti-angiogenesis compounds, cytotoxins directly into or onto tumors, where agents are optionally delivered in controlled release formulation or configuration; b) using the apparatus for controlled delivery of tissue engineering scaffold agents, growth factors, and cells to i) facilitate wound healing in chronic sores, ii) provide a matrix for chrondorcytes growth in damaged articular cartilage, or iii) repair of arterial walls following angioplasty or other trauma; c) fabrication of matrices with the fiber optic device placed against the gingiva in order to effect photo-optical fabrication directly in the sulcus space, to deliver and attach antibacterial agents, growth factors and other agents to diseased tissue in a minimally invasive approach, or to deliver therapeutic agents to diseased and damaged gingival and other epithelial lesions, to kill tumors, and to promote heaiing of chronic wounds, d) in situ photodynamic therapy, as disclosed, for example, by J. Bhawalkar and N. Kumar et al. in "Two-Photon Photodynamic Therapy," Journal of Clinical Laser Medicine & Surgery, Vol. 15, pp. 201–204(1997); e) in situ fabrication of matrixes for, for example, the guided regeneration of articular cartilage and/or simultaneous entrapment of chondrocytes into the regeneration matrix, f) fabrication of scaffolds for epithelial wound repair in skin, cornea and other tissues at, or below the surface, g) assembly of minimally invasive scaffolds in situ to restore, effect repairs, or strengthen tendon and ligament IV attachment, h) site directed repair and rebuilding of anuretic or hemorrhagic arteries via minimally invasive reconstruction for cardiovascular medicine, i) delivery of controlled release pharmaceutics and bioactive agents to plagues, tumors, lesions, and chronic wounds; and j) minimally invasive assembly of structural elements or devices such as stents.

Configuration for fiber coupling into a fiber optic is straightforward for continuous wave or nanosecond pulsed lasers, but is much more complex for femtosecond lasers. Both group velocity dispersion (GVD) and self-phase modulation (SPM) must be considered in coupling short laser pulses. GVD occurs when light travels through a dispersive medium such as a silica fiber. For monochromatic light, this issue is negligible. However, a 100 femtosecond laser pulse has a spectral width of about 10 nm full width half maximum (FWHM), and its components typically have different refractive indices in a fiber, resulting in a positive frequency "chirp" where the red components travel faster than the blue components After propagating though a long fiber, the pulse is broadened out to a few picoseconds. SPM results when a spectrally broad pulse of high peak power is focused tightly, as into a 10 micron single mode polarization preserving fiber. The peak power modulates the refractive index and adds frequency components to the red and blue, and the 10 nm spectral width considerably broadens. The solution is to pre-chirp the pulse with a grating pair, which provide negative dispersion, reducing the peak power and thereby minimizing SPM. The positive dispersion of the fiber probe will then recompress the pulse to near 100 femtoseconds. Both second and third order dispersion can be compensated through this process with the proper choice of optics and was recently demonstrated by Lewis et al. Since a microscope is an integral part of the apparatus for practice of this embodiment, precise placement of a multi-photon-fabricated feature or device on a surface or in tissues is readily achievable.

The above-described embodiments may also be combined as desired in order to create complex devices and structures. For example, devices with a combination of enzymes, motile proteins and optical properties may be used for biosensor applications. Fiber optic fabrication systems may be used for catheter-driven repair of tissue damage or to deliver biodegradable compounds to effect tumor killng.

The invention is further illustrated by the following non-limiting Examples.

Apparatus

Figure 21:
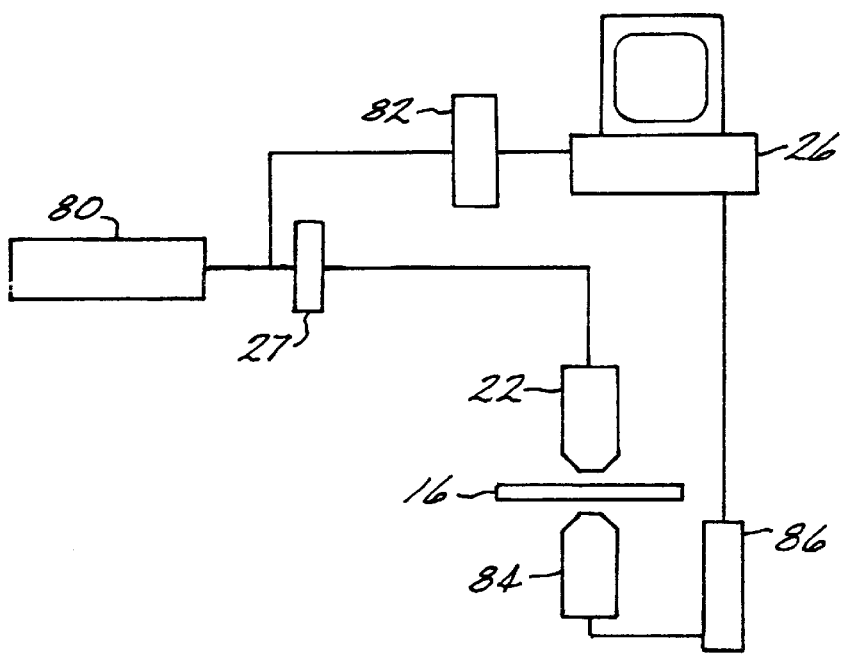
FIG. 21 a schematic diagram of the apparatus used in the present invention.

The apparatus used in the following Examples is shown schematically in FIG. 21. It comprises a modified BioRad laser scanning confocal microscope (BioRad MRC 600) having a computer 26, galvoscanner 27, and a 0.5–1.4 objective lens 22 for focus on stage 16. Fabrication is monitored using florescence detection via photomultiplier tube 82 and/or the condenser lens 84 and photomultiplier tube 86. The microscope is fitted with a femtosecond titanium: sapphire laser 80 (Coherent Mira 900-F).

EXAMPLE 1

Reaction of UV-Activated Polyurethane-Based Adhesive Precursor System

A polyurethane-based optical adhesive precursor system was obtained from Norland Products Inc., N. Brunswick, N.J. having the trade name Norland Optical Adhesive 83H. This adhesive system is ordinarily activated by exposing the adhesive precursor to UV light at 320–380 nm with peak intensity at 365 nm. Adhesive precursor was placed on a microscope slide on a stage which could be manually scanned in the X-Y plane. A focused beam was scanned on the precursor at a wavelength of 790 or 785 nm and pulse lengths of 100 femtoseconds and average power of 10 milliwatts (mW) at 76 megahertz (MHZ) repetition rate. The galvanometer scanner of the DioRad laser scanning confocal microscope was used to direct the focused diffraction limited spot along a line about 600 microns long through a 0.5 or 0.75 NA 20 times magnification Zeiss Neofluor objective. To effect fabrication, the scan line was drawn and redrawn a minimum of about 100 times. The rod was fabricated quickly, in about 1–2 seconds. After fabrication, unreacted resin was removed from the structure by washing with ethanol and acetone. The sample was then air dried and sputter coated with 10 nm of AuPd in preparation for scanning electron microscopy.

FIG. 5 is an SEM image of several polyurethane rods manufactured by the above method. FIG. 6 is a scanning electron micrograph of a polyurethane sheet manufactured by the above method (the folding of the sheet is an artifact of SEM sample preparation). FIGS. 7A and 7B show pyramidal structures.

EXAMPLE 2

Polymerization of Bovine Serum Albumin (BSA)

Bovine serum albumin was dissolved in water to a concentration of 10 mg/L. One mL of the BSA solution was then made about $1 \times 10^{-4}$ in the photoinitiator Rose Bengal. This solution was then subjected to two-photon excitation as described in Example 1, resulting in polymerization. TEA may be present, but slows the reaction. FIGS. 12 and 14 show rods and pyramides, respectively, fabricated by two-photon excitation.

For three-photon excitation, the above solution was prepared, except for the substitution of Rose Bengal about 1 milligram (mg) of 9-fluorenone-2-carboxylic acid. Another aliquot of this solution was placed on a microscope slide on the stage, and a focused beam was scanned on the solution at a wavelength of 780 nm and pulse lengths of 100 femtoseconds. The galvanometer scanner of the BioRad laser scanning confocal microscope was used to direct the focused spot along a line about 600 microns long. A 0.5 NA 20X Zeiss Neofluor objective was used. Average power levels were 130 mW at 76 MHZ repetition rate, as measured without the objective lens in place, with an estimated energy loss through the objective of about 25 mW. Fabrication required the scan line to be drawn and redrawn a minimum of about 100 times, for a total dwell time required for optically visible fabrication of about 1–2 seconds. The 780 nm wavelength represents a three-photon excitation of the fluorenone photoinitiator, which has a one-photon absorption maximum for the $\pi \rightarrow \pi^*$ transition of about 270 nm. Upon excitation to the singlet state the fluorenone rapidly converts to the triplet state and initiates crosslinking via hydrogen abstraction. Two possible mechanisms are as follows:

(1) Fluorenone (triplet)+BSA→BSA.+H
BSA*+BSA→(BSSA)$_2$.
(BSA)$_2$.+BSA→(BSA)$_3$. etc.
(2) Fluorenone (triplet)+TEA→TEA.+H
TEA.+BSA→BSA.+TEA
BSA.+BSA→(BSA)$_2$.
(BSA)$_2$.+BSA→(BSA)$_3$. etc.

The increased kinetic stability of the txiethanolamine radical may contribute to increasing the efficiency of the crosslinking reaction. FIGS. 13A (lower magnification) and 13B (higher magnification) are SEM images of a rod manufactured by three-photon polymerization of BSA, wherein the diameter of the rod is about 500 nm.

EXAMPLE 3

Polymerization of Trimethyloipropane Trimethacrylate

Trimethylolpropane trimethacrylate (Aldrich) was made $1 \times 10^{-5}$ in Rose Bengal, 0.1 M in triethanolamine, with about a drop of dimethyl sulfoxide (DMSO) added to enhance solubility. An acqlate polymer in the form of a pyramid (FIG. 10) was formed using a two-photon process as described for Example 1.

Substitution of Rose Bengal with $2 \times 10^{-5}$ 9-fluorenone-2-carboxylic acid in the above reaction mixture resulted in polymerization upon treatment using three-photon excitation as described in Example 2. A lamellar structure formed by this method is shown in FIG. 9, comprising five stacked layers of polymerized trimethylolpropane trimethacrylate (the object is rotated about 85 degrees from the horizontal). The top two layers were peeled back during SEM sample preparation to reveal the inner layers.

EXAMPLE 4

Polymerization of Acrylamide

A 40% aqueous solution comprising a ratio of acrylamide:bisacrylamide was made $1 \times 10^{-4}$ in Rose Bengal and 0.1 M in triethanolamine. A polyacrylaride polymer in the form of a pyramid (FIG. 10) was formed using the two-photon process as described for Example 1. Acrylamide gels are useful for entrapment of bioactive and other compounds for sustained release.

EXAMPLE 5

Polymerization of Fibrinogen

An aqueous solution comprising 5 mg/mL of fibrinogen and $1 \times 10^{-4}$ Rose Bengal was polymerized using two-photon excitation as described in Example 1. Polymerization was also effected by two-photon excitation in the presence of Rose Bengal, but without triethanolamine.

EXAMPLE 6

Short Term Entrapment of an Agent in a Fabricated Matrix

Figure 22:
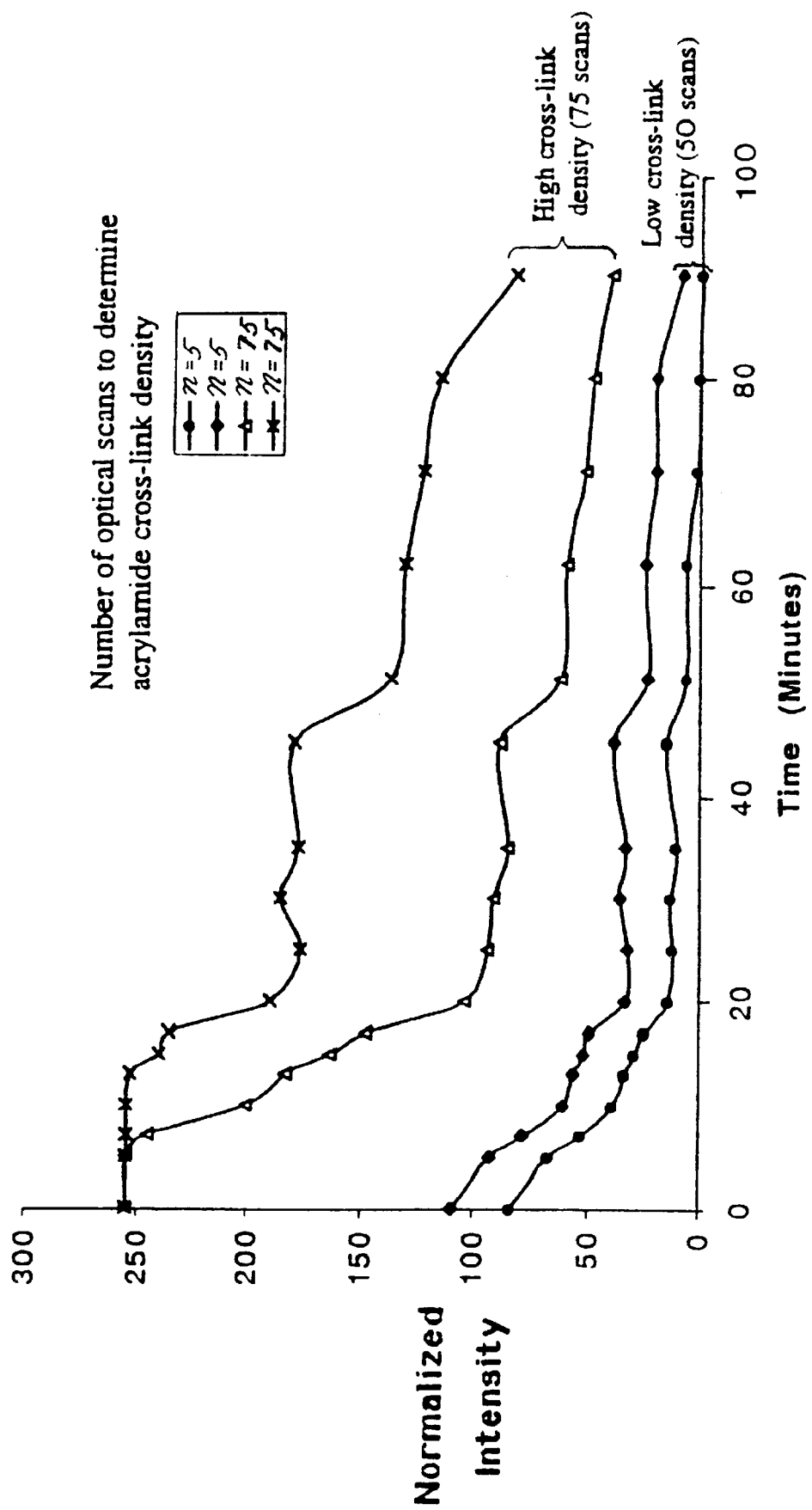
FIG. 22 is a graph showing release of rhodamine from a polyacrylamide gel.

Short term entrapment of an agent in a matrix fabricated by multi-photon excitation was illustrated with polyacrylamide gel/Rhodamine 610 and a BSA matrix/dextran. The polyacrylamide gel was formed by two-photon activation of a 17.5% aqueous solution containing a 29:1 ratio of acrylamide: bisacrylamide, $1\times10^{-4}$M rose Bengal, 0.1 M triethanolomine, and loaded with $2\times10^{-3}$ M Rhodamine 610. The formed gels were approximately 70 microns×100 micron×1.5 mnicrons, and possessed different crosslink densities obtained by varying the irradiation time via the number of successive scans performed (50 and 75). The release of Rhodamine 610 was monitored optically by integration of the fluorescence intensity over the rectangular gels. As the data from two replicant experiments illustrated in FIG. 22 shows, higher crosslink densities results in slower Rhodamine release.

Figure 23:
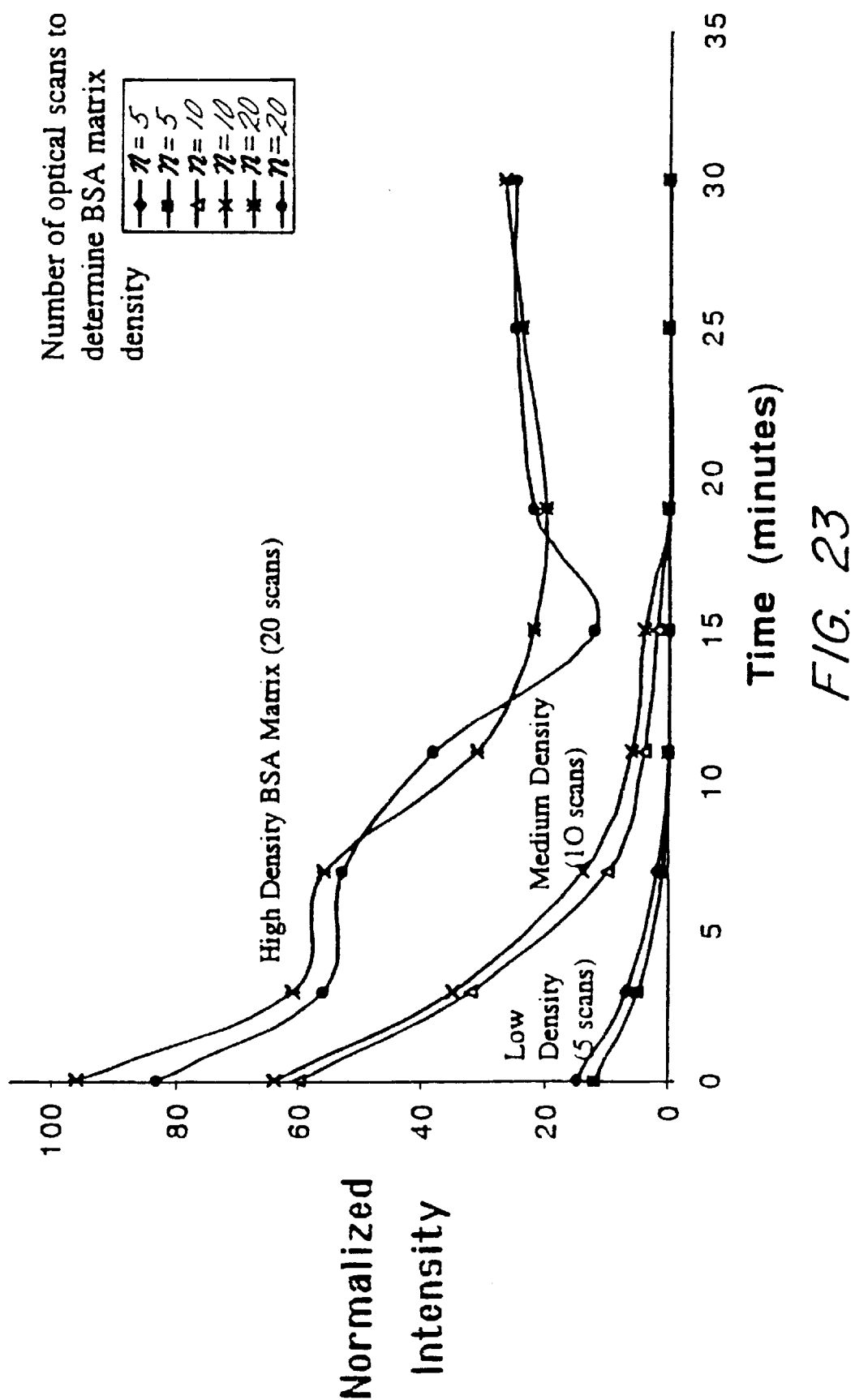
FIG. 23 is a graph showing release of rhodamine-labeled dextran from a crosslinked BSA matrix.

The BSA matrix was fabricated by two-photon activation of an aqueous solution comprising 10 mg/nm BSA, $1\times10^{-4}$ rose Bengal, and loaded with $1\times10^{-4}$M tetramethyl rhodamine labeled 10 kilodalton (kD) dextran (Molecular Probes, Eugene, Oreg.). The rectangular BSA matrices were approximately 140 micron×175 micron×1.5 micron, and had different cross link densities due to using differing numbers of successive scans to form the matrix (5, 10, and 20). The release of 10 kD dextran was monitored optically by integration of the fluorescence intensity over the rectangular gels. Data from two replicant experiments is shown in FIG. 23, which indicates that greater crosslink densities result in slower agent release.

EXAMPLE 7

Long Term Entrapment of Alkaline Phosphatase

Permanent or long-term entrapment of a reactive agent such as an enzyme allows diffusion of a soluble reactant into a gel or construct, which is then acted upon by the entrapped agent. In this example, entrapment of alkaline phsophatase results in removal of a phosphate moiety from the soluble reactant. Alkaline phosphatase was chosen as a model enzyme since its activity may be readily assayed and spatially localized with fluorescence microscopy using an enzyme-linked fluorescence (ELF) reagent produced by Molecular Probes Inc. (B6601, Eugene, Oreg.). Upon cleavage of the phosphate group from the ELF reagent, its fluorescent emission wavelength changes, its fluorescent intensity greatly increased, and it became insoluble, thereby precipitating in the immediate vicinity of the active enzyme. Images were produced by excitation of the precipitated agent by 2-photon excitation fluorescence at about 825 nm.

Figure 24:
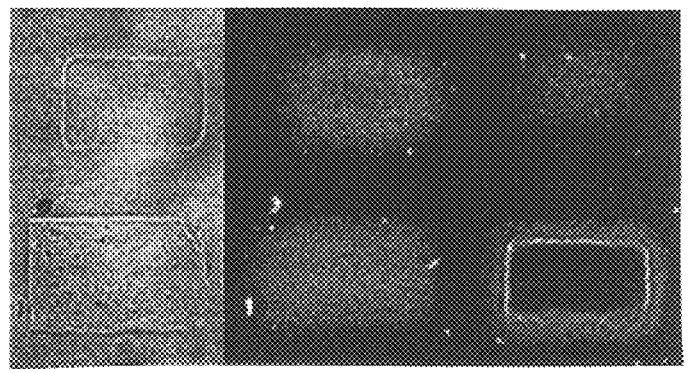
FIGS. 24A–C shows gels having entrapped alkaline phosphatase, wherein 23A is a transmitted light image and 23B and 23C are fluorescence images of enzyme activity as indicated by enzyme-linked fluorescence. The acrylamide in the lower gel was optically fabricated with a greater crosslink density.

Accordingly, alkaline phosphatase (Sigma P-0530) was incorporated into rectangularpolyacrylamide gels (134 micron×89 micron×15 micron) by two-photon excitation of a 40% aqueous solution of 29:1 acrylamide :bisacrylamide, comprising $1\times_{10}^{-4}$ rose Bengal, 0.1 M triethanolamine, and 2 micromolar bovine alkaline phosphatase. Varying the time of polymerization resulted in gels having different densities. One gel received 50 scans (total photon dose=$2\times10^{\circ}$photons/$cm^2$) and the another gel received 75 scans (photon dose= $3\times10^{20}$ photons/$cm^2$), with this higher photon dose leading to a slightly larger polymerized area, due to oversaturation-induced decreased confinement of the two-photon excitation zone, FIG. 24A shows the gels by transmitted light, and FIGS. 24B and 24C are fluorescence images. The acrylamide in the lower gel was optically fabricated with a greater crosslink density. FIG. 24B shows that enzyme activity at 30 minutes is fairly uniform in both gels with a focal plane near the top, while FIG. 24C shows less enzyme activity in the center of the higher crosslink density gel (lower gel) at a focal plane close to the glass substrate (60 minutes). The higher density gel thus inhibits diffusion of the ELF reagent into the gel from the edges.

Figure 25:
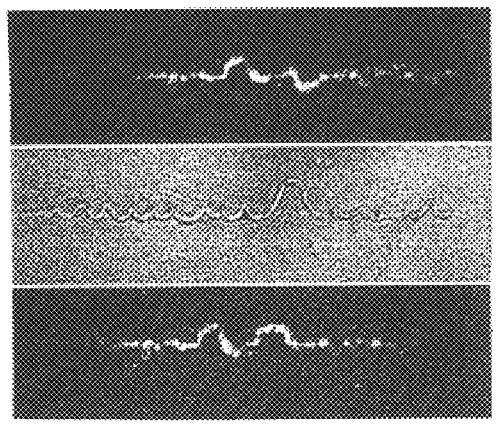
FIGS. 25A–C show a single alkaline phosphatase-loaded acrylamide fiber wherein each fiber is approximately 350 nm in diameter.

Encapsulation may also be accomplished with smaller constructs. FIGS. 25A–C show a single alkaline phosphatase-loaded acrylamide fiber wherein each fiber is approximately 350 nm in diameter. FIGS. 25A and 25C show ELF fluorescence about 30 minutes apart, and FIG. 25B is a transmitted light image. Observations over time indicate that the fiber configuration changes, which is not surprising in that the fibers are not flexible and are not tightly adhered to the substrate. Images also indicate that enzyme activity is decreased in regions where the fiber is in closer contact with the substrate (the left and right-hand sides of the fiber). It is theorized that diffusion of ELF reagent is inhibited in these regions.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for the fabrication of a small structure, comprising providing a photoactivatable precursor composition;

activating the precursor composition using multi-photon excitation in at least one first location in the precursor composition to form at least one first portion of the small structure, wherein the at least one first portion has dimensions in the X-Y directions of less than about 300 nanometers.

2. The method of claim 1, wherein the at least one first portion has a dimension in the Z direction of less than about 500 nanometers.

3. The method of claim 1, wherein the at least one portion has dimensions in the X-Y direction of less than about 250 nanometers.

4. The method of claim 3, wherein the at least one first portion has a dimension in the Z direction in the range of less than about 300 nanometers.

5. The method of claim 3, wherein the at least one portion has a dimension in the Z direction of less than about 100 nanometers.

6. The method of claim 1, wherein the at least one first portion has dimensions in the X, Y, and Z directions of less than about 50 nanometers.

7. The method of claims 1, wherein the photoactivatable precursor composition comprises photoactivatable precursors selected from the group consisting of photopolymerizable organic monomers, photopolymerizable inorganic monomers, cross-linkers, monomers having at least one olefinic bond, oligomers having at least one olefinic bond, polymers having at least one olefinic bond, olefins, halogenated olefins, acrylates, methacrylates, acrylamides, bisacrylamides, styrenes, epoxides, cyclohexeneoxide, amino acids, peptides, proteins, fatty acids, lipids, nucleotides, oligonucleotides, synthetic nucleotide analogues, nucleic acids, sugars, carbohydrates, cytokines, hormones, receptors, growth factors, drugs, and mixtures thereof.

8. The method of claim 7, wherein the photoactivatable precursor composition comprises photoactivatable precursors selected from the group consisting of proteins, fibrinogen, bovine serum albumin, trimethylolpropane triacrylate, and polyurethane precursors.

9. The method of claim 7, wherein the precursor is a protein.

10. The method of claim 7, wherein the precursor composition further comprises a photoinitiator.

11. The method of claim 10, wherein the photoinitiatot is selected from the group consisting of azo compounds, azobisisobutyronitrile, peroxides, benzoyl peroxide, aliphatic ketones and diketones, aromatic diketones, benzophenone, 9-fluorenone 2-carboxylic acid, ion pairs, the ion pair $Fe^{3+}OH^-$, the ion pair $Pb^{2+}Cl^-$), photosensitive dyes, eosin, rose Bengal, erydirosin, photosensitive transition metal derivatives, and $Mn_2(CO)_{10}$ in the presence of organic halides, triarylsulfonium salts with complex metal halide anions, diaryliodonium salts with complex metal halide anions, mixed arene cyclopentadienyl metal salts of complex metal halide anions, and (6-benzene)(5-cyclopentadienyl)Fe(II) hexafluorophosphate.

12. The method of claim 1, wherein activation is in bulk, in solution, adsorbed to a substrate, in suspension, or an emulsion.

13. The method of claim 1, wherein activation is by two-photon, three-photon, or four-photon excitation.

14. The method of claim 1, wherein activation results in polymerization or cross-lining of the precursor composition.

15. The method of claim 1, wherein the first portion is fabrication from a first precursor composition and a second portion is fabricated from a second precursor composition.

16. The method of claim 1, wherein the first portion is fabricated at a first wavelength, and a second portion is fabricated at a second wavelength.

17. A method for the fabrication of a small structure, comprising
providing a photoactivatable precursor composition;
activating the precursor composition using multi-photon excitation in at least one first location in the precursor composition to form at least one first portion of the small structure, wherein the point volume of the first portion has dimensions of less than about 1 micron.

18. The method of claim 17, wherein the point volume of the first portion has at least one dimension of less than about 500 nm.

19. The method of claim 17, wherein the point volume of the first portion has at least one dimension of less than about 250 nm.

20. The method of claim 17, wherein the point volume of the first portion has at least one dimension of less than about 100 nm.

21. The method of claim 17, wherein the point volume of the first portion has at least one dimension of less than about 50 nm.

22. The method of claim 17, wherein the photoactivatable precursor composition comprises photoactivatable precursors selected from the group consisting of photopolymerizable organic monomers, photopolymerizable inorganic monomers, cross-linkers, monomers having at least one olefinic bond, oligomers having at least one olefinic bond, polymers having at least one olefinic bond, olefins, halogenated olefins, acrylates, methacrylates, acrylamides, bisacrylamides, styrenes, epoxides, cyclohexeneoxide, amino acids, peptides, proteins, fatty acids, lipids, nucleotides, oligonucleotides, synthetic nucleotide analogues, nucleic acids, sugars, carbohydrates, cytokines, hormones, receptors, growth factors, drugs, and mixtures thereof.

23. The method of claim 22, wherein the photoactivatable precursor composition comprises photoactivatable precursors selected from the group consisting of proteins, fibrinogen, bovine serum albumin, trimethylolpropane triacrylate, and polyurethane precursors.

24. The method of claim 22, wherein the precursor is a protein.

25. The method of claim 22, wherein the precursor composition further comprises a photoinitiator.

26. The method of claim 25, wherein the photoinitiator is selected from the group consisting of azo compounds, azobisisobutyronitrile, peroxides, benzoyl peroxide, aliphatic ketones and diketones, aromatic diketones, benzophenone, 9-fluorenone 2-carboxylic acid, ion pairs, the ion pair $Fe^{3+}OH^-$, the ion pair $Pb^{2+}Cl^-$, photosensitive dyes, eosin, rose Bengal, erythrosin, photosensitive transition metal derivatives, and $Mn_2(CO)_{10}$ in the presence of organic halides, triarylsulfonium salts with complex metal halide anions, diatyliodonium salts with complex metal halide anions, mixed arene cyclopentadienyl metal salts of complex metal halide anions, and (6-benzene)(5-cyclopentadienyl)Fe(II) hexafluorophosphate.

27. The method of claim 17, wherein activation is in bulk, in solution, adsorbed to a substrate, in suspension, or an emulsion.

28. The method of claim 17, wherein activation is by two-photon, three-photon, or four-photon excitation.

29. The method of claim 17, wherein activation results in polymerization or cross-linking of the precursor composition.

30. The method of claim 17, wherein the first portion is fabrication from a first precursor composition and a second portion is fabricated from a second precursor composition.

31. The method of claim 17, wherein the first portion is fabricated at a first wavelength, and a second poon is fabricated at a second wavelength.

32. A method for entrapping an agent within a construct, comprising
providing a photoactivatable precursor composition comprising at least one construct precursor and at least one agent;
activating the precursor composition using multi-photon excitation in at least one first location in the precursor composition to form at least one first portion of the construct, wherein the at least one first portion has dimensions in the X-Y directions of less than about 300 nanometers, wherein the agent is entrapped within the construct.

33. The method of claim 32, wherein the agent is selected from the group consisting of growth factors, nucleotides, ions, buffering agents, dyes, proteins, peptides, enzymes, carbohydrates, glycosaminoglycans, nucleotides, liposomes, cells, drugs, and combinations thereof.

34. The method of 32, wherein the construct has controlled release properties, controlled degradation properties, controlled diffisivity properties, or a combination thereof.

35. The method of claim 34, wherein diffusion or release properties are controlled by control of the affinity of the agent for the construct, the degree of crosslink density of the construct, the rate of degradation of the construct, the composition of the construct, or a combination thereof.

36. The method of claim 35, wherein control of the degree of affinity of the agent for the construct is by appropriate selection of backbone and/or crosslink compositions.

37. The method of claim 35, wherein control of the cross-link or polymerization density is by varying illumination time, intensity (photon energy density), constructs spatial dimensions, addition of overlayers without entrapped reagents, by three-dimensional patterning, or by combinations thereof.

38. The method of claim 32, wherein the at least one first portion has a dimension in the Z direction of less than about 500 nanometers.

39. The method of claim 32, wherein the at least one portion has dimensions in the X-Y direction of less than about 250 nanometers.

40. The method of claim 39, wherein the at least one first portion has a dimension in the Z direction in the range of less than about 300 nanometers.

41. The method of claim 39, wherein the at least one portion has a dimension in the Z direction of less than about 100 nanometers.

42. The method of claim 32, wherein the at least one first portion has dimensions in the X, Y, and Z directions of less than about 50 nanometers.

43. The method of claim 32, wherein the photoactivatable precursor composition comprises photoactivatable precursors selected from the group consisting of photopolymerizable organic monomers, photopolymerizable inorganic monomers, crosslinkers, monomers having at least one olefinic bond, oligomers having at least one olefinic bond, polymers having at least one olefinic bond, olefins, halogenated olefins, acrylates, methacrylates, acrylamides, bisacrylamides, styrenes, epoxides, cyclohexeneoxide, amino acids, peptides, proteins, fatty acids, lipids, nucleotides, oligonucleotides, synthetic nucleotide analogues, nucleic acids, sugars, carbohydrates, cytokines, hormones, receptors, growth factors, drugs, and mixtures thereof.

44. The method of claim 43, wherein the photoactivatable precursor composition comprises photoactivatable precursors selected from the group consisting of proteins, fibrinogen, bovine serun albumin, trimethylolpropane triacrylate, and polyurethane precursors.

45. The method of claim 43, twherein the precursor is a protein.

46. The method of claim 43, wherein the precursor composition further comprises a photoinitiator.

47. The method of claim 46, wherein the photoinitiator is selected from the group consisting of azo compounds, azobisisobutyronitrile, peroxides, benzoyl peroxide, aliphatic ketones and diketones, aromatic diketones, benzophenone, 9-fluorenone 2-carboxylic acid, ion pairs, the ion pair $Fe^{3+}OH^-$, the ion pair $Pb^{2+}Cl^-$), photosensitive dyes, eosin, rose Bengal, erytlirosin, photosensitive transition metal derivatives, and $Mn_2(CO)_{10}$ in the presence of organic halides, triarylsulfonium salts with complex metal halide anions, diaryliodonium salts with complex metal halide anions, mixed arene cyclopentadienyl metal salts of complex metal halide anions, and (6-benzene)(5-cyclopentadienyl)Fe(II) hexafluorophosphate.

48. The method of claim 32, wherein activation is in bulk, in solution, adsorbed to a substrate, in suspension, or an emulsion.

49. The method of claim 32, wherein activation is by two-photon, three-photon, or four-photon excitation.

50. The method of claim 32, wherein activation results in polymerization or cross-linking of the precursor composition.

51. The method of claim 32, wherein the first portion is fabrication from a first precursor composition and a second portion is fabricated from a second precursor composition.

52. The method of claim 32, wherein the first portion is fabricated at a first wavelength, and a second portion is fabricated at a second wavelenght.

53. A method for entrapping an agent within a construct, comprising providing a photoactivatable precursor composition;

activating the precursor composition using multi-photon excitation in at least one first location in the precursor composition to form at least one first portion of the construct, wherein the at least one first portion has dimensions in the X-Y directions of less than about 300 nanometers;

forming the remainder of the construct; and entrapping the agent within the formed construct.

54. The method of claim 53, wherein the agent is selected from the group consisting of growth factors, nucleotides, ions, buffering agents, dyes, proteins, peptides, enzymes, carbohydrates, glycosaminoglycans, nucleotides, liposomes, cells, drugs, and combinations thereof.

55. The method of claim 53, wherein the agent is selected from the group consisting of entrapped enzymes that continuously act on molecules which diffuse into the gel or construct before the molecules diffulse out of the gel or construct; enzymes, chelators, or other molecules which act on molecules which diffuse into the gel, and through this action become unable to leave the gel or construct; motile proteins, peptides, or non-biochemical structures which cause the fabricated construct to wiggle, change shape, or change its diffusion properties when specific molecules, ions, or others agents diffuise into the gel; photodynamic molecules which change color, refraction, diffusion, transport, shape, or other physical properties or biochemical activities when illuminated at certain wavelengths, polarizations, or other states of light; entrapped chemoactive molecules which change color, refraction, diffusion, transport or other physical and/or biochemical properties due to the activity of chemical agents which diffuise into a gel or other construct such as ions, pH, and biomolecules; proteins for nano-Ochterlony-like immunodiffuision assays; living cells; or combinations thereof.

56. The method of claim 55, wherein the proteins or cells are entrapped by encapsulation, covalent cross-linking with the construct, or a combination thereof.

57. The method of claim 53, wherein the at least one first portion has a dimension in the Z direction of less than about 500 nanometers.

58. The method of claim 53, wherein the at least one portion has dimensions in the X-Y direction of less than about 250 nanometers.

59. The method of claim 58, wherein the at least one first portion has a dimension in the Z direction in the range of less than about 300 nanometers.

60. The method of claim 58, wherein the at least one portion has a dimension in the Z direction of less than about 100 nanometers.

61. The method of claim 53, wherein the at least one first portion has dimensions in the X, Y, and Z directions of less than about 50 nanometers.

62. The method of claim 53, wherein the photoactivatable precursor composition comprises photoactivatable precursors selected from the group consisting of photopolymerizable organic monomers, photopolymerizable inorganic monomers, cross-linkers, monomers having at least one olefinic bond, oligomers having at least one olefinic bond, polymers having at least one olefinic bond, olefins, halogenated olefins, acrylates, methacrylates, acrylamides, bisacrylamides, styrenes, epoxides, cyclohexeneoxide, amino acids, peptides, proteins, fatty acids, lipids, nucleotides, oligonucleotides, synthetic nucleotide analogues, nucleic acids, sugars, carbohydrates, cytokines, hormones, receptors, growth factors, drugs, and mixtures thereof.

63. The method of claim 62, wherein the photoactivatable precursor composition comprises photoactivatable precursors selected from the group consisting of proteins, fibrinogen, bovine serum albumin, trimethylolpropane triacrylate, and polyurethane precursors.

64. The method of claim 62, wherein the precursor is a protein.

65. The method of claim 62, wherein the precursor composition further comprises a photoinitiator.

66. The method of claim 65, wherein the photoinitiator is selected from the group consisting of azo compounds, azobisisobutyronitrile, peroxides, benzoyl peroxide, aliphatic ketones and diketones, aromatic diketones, benzophenone, 9-fluorenone 2-carboxylic acid, ion pairs, the ion pair $Fe^{3+}OH^-$, the ion pair $Pb^{2+}Cl^-$), photosensitive dyes, eosin, rose Bengal, erythrosin, photosensitive transition metal derivatives, and $Mn_2(CO)_{10}$ in the presence of organic halides, triarylsulfonium salts with complex metal halide anions, diaryliodonium salts with complex metal halide anions, mixed arene cyclopentadienyl metal salts of complex metal halide anions, and (6-benzene)(5-cyclopentadienyl)Fe(II) hexafluorophosphate.

67. The method of claim 53, wherein activation is in bulk, in solution, adsorbed to a substrate, in suspension, or an emulsion.

68. The method of claim 53, wherein activation is by two-photon, three-photon, or four-photon excitation.

69. The method of claim 53, wherein activation results in polymerization or cross-linking of the precursor composition.

70. The method of claim 53, wherein the first portion is fabrication from a first precursor composition and a second portion is fabricated from a second precursor composition.

71. The method of claim 53, wherein the first portion is fabricated at a first wavelength, and a second portion is fabricated at a second wavelength.

72. A method for modifying the surface of a material, comprising
providing a photoactivatable precursor composition and a surface;
activating the precursor composition using multi-photon excitation in at least one first location in the precursor composition to form at least one first portion of a construct, wherein the at least one first portion has dimensions in the X-Y directions of less than about 300 nanometers, and wherein the at least one first portion is covalently linked to the surface.

73. The method of claim 72, wherein the surface is the surface of an integrated chip.

74. The method of claim 73, wherein the surface comprises bovine serum albumin which has been crosslinked by multiphoton excitation, and the construct photoactivatable precursor comprises fibrinogen.

75. The method of claim 73, wherein the modified surface provides a scaffold for tissue cell culture.

76. The method of claim 73, wherein the surface is modified by attachment to at least one motile protein.

77. The method of claim 76, wherein the motile protein is selected from the group consisting of kinesin, microtubules, actin, axonemes, flagella, or a combination thereof.

78. A method for manufacture of the surface of sensor array chip, comprising
providing a photoactivatable precursor composition and a chip surface;
activating the precursor composition using multi-photon excitation in at least one first location in the precursor composition to form at least one first portion of a sensor, wherein the at least one first portion has dimensions in the X-Y directions of less than about 300 nanometers, and wherein the at least one first portion is covalently linked to the chip surface.

79. A method for provide spatial orientation of an agent, comprising
providing a photoactivatable precursor composition and a first agent;
activating the precursor composition using multi-photon excitation in at least one first location in the precursor composition to form at least one first portion of a construct, wherein the at least one first portion has dimensions in the X-Y directions of less than about 300 nanometers, and wherein the at least one first portion is covalently linked to the agent;
repeating the activation with a second agent, such that the second agent is spatially arrayed relative to the first agent.

80. The method of claim 79, wherein the agent first and second agents are selected from the group consisting of enzymes, antibodies, receptors, ribosomes and combinations thereof.

81. The method of claim 80, wherein the first and second agents perform biochemical synthesis, or perform separations.

82. The method of claim 80, wherein the second agent is arrayed by self-assembly, application of electrostatic fields, magnetic fields, shear forces, laser tweezers, magnetic tweezers, and combinations thereof.

83. A method for modifying explanted tissue, comprising
providing a photoactivatable precursor composition and explanted tissue;
activating the precursor composition using multi-photon excitation in at least one first location in the precursor composition to form at least one first portion of a construct, wherein the at least one first portion has dimensions in the X-Y directions of less than about 300 nanometers, and wherein the at least one first portion is covalently linked to the explanted tissue.

84. The method of claim 83, wherein the construct crosslinks the tissue, links chelating agents or antibacterial agents to the tissue, or a combination thereof.

85. A method for the manufacture of a form for multiple production, comprising
providing a photoactivatable precursor composition;
activating the precursor composition using multi-photon excitation in at least one first location in the precursor composition to form at least one first portion of a the form, wherein the at least one first portion has dimensions in the X-Y directions of less than about 300 nanometers.

86. The method of claim 85, wherein the form is a mold, stamper, mask, or mask for photolithography.

87. A method for the manufacture of complex three-dimensional forms, comprising
providing a photoactivatable precursor composition which undergoes dynamic shape change upon fabrication;

activating the precursor composition using multi-photon excitation in at least one first location in the precursor composition to form at least one first portion of a the form, wherein the at least one first portion has dimensions in the X-Y directions of less than about 300 nanometers.

88. A method for the manufacture of complex three-dimensional forms, comprising providing a photoactivatable precursor composition which undergoes dynamic shape change upon exposure to a change in environment;

activating the precursor composition using multi-photon excitation in at least one first location in the precursor composition to form at least one first portion of a the form, wherein the at least one first portion has dimensions in the X-Y directions of less than about 300 nanometers.

89. The method of claim 88, wherein the change in environment is a change in temperature, solvent, ionic strength, presence of a ligand, or a combination thereof.

* * * * *

UNITED STATES PATENT AND TRADEMARK OFFICE
CERTIFICATE OF CORRECTION

PATENT NO.    : 6,316,153 B1
DATED         : November 13, 2001
INVENTOR(S)   : Steven L. Goodman et al.

It is certified that error appears in the above-identified patent and that said Letters Patent is hereby corrected as shown below:

Title page, Item [54] and Column 1, line 1,
Title, after "FREE-FORM" delete "FABRICATON" and insert -- FABRICATION --.

Title page,
Item [57], ABSTRACT,
Line 14, after "300" delete "mn" and insert -- nm --;
Line 17, after "250" delete "mn" and insert -- nm --.

Column 1,
Line 62, after "three-dimensional" delete "bionminetic" and insert -- biomimetic --.

Column 2,
Line 36, after "to" delete "near-irfrared" and insert -- near-infrared --;
Line 44, after "there" delete "stiff" and insert -- still --;
Line 57, after "and/or" delete "cross-linning" and insert -- cross-linking --;
Line 62, before "preferably" delete "mincron" and insert -- micron --.

Column 3,
Line 7, after "of a" delete "4 pi" and insert -- 4Pi --;
Line 25, after "and/or" delete "diffisivity" and insert -- diffusivity --;
Line 37, after "to the materials" delete "to the materials".

Column 4,
Line 24, after "field" delete "4 pi" and insert -- 4Pi --;
Line 55, after "magnifications", insert -- . --.

Column 7,
Line 45, after "less" delete "rs";
Line 53, after "aperture" delete "(A)" and insert -- (NA) --;
Line 59, after "of a" delete "4 pi" and insert -- 4Pi --;
Line 64, before "optics" delete "4 Pi" and insert -- 4Pi --;
Line 66, after "with a" delete "4 Pi-Confocal" and insert -- 4Pi-Confocal --.

Column 8,
Line 13, after "from" delete "ether bean" and insert -- either beam --;
Line 14, before "optics" delete "4 Pi" and insert -- 4Pi--.

UNITED STATES PATENT AND TRADEMARK OFFICE
CERTIFICATE OF CORRECTION

PATENT NO. : 6,316,153 B1
DATED : November 13, 2001
INVENTOR(S) : Steven L. Goodman et al.

It is certified that error appears in the above-identified patent and that said Letters Patent is hereby corrected as shown below:

Column 9,
Line 17, after "most" delete "organicl" and insert -- organic/--;
Line 34, after "polymer." delete "la".

Column 11,
Line 6, after "been" delete "is";
Line 23, after "or" delete "crosslining" and insert -- crosslinking --;
Line 47, after "or" (second occurrence) delete "crosslieing" and insert -- crosslinking --.

Column 12,
Line 11, after "bioactive)" insert -- agents --;
Line 14, after "controlled" delete "diffuisivity" and insert -- diffusivity --;
Line 19, after "and" delete "and";
Line 51, after "in" delete "polyacrylaride" and insert -- polyacrylamide --.

Column 13,
Line 6, after "entrapped" delete "photodynaric" and insert -- photodynamic --;
Line 38, before "of the" delete "cross-llnning" and insert -- cross-linking --;
Line 47, after "directly" delete "cross-inking" and insert -- cross-linking --;

Column 14,
Line 42, after "multi-photon" delete "exdtation" and insert -- excitation --;
Line 47, before "for" delete "usefl" and insert -- useful --.

Column 15,
Line 15, after "effecting" delete "cross-lking" and insert -- cross-linking --.

Column 16,
Line 1, before "effects" delete "shrinkage|expansion" and insert -- shrinkage/expansion --;
Line 19, after "active" delete "finctionality" and insert -- functionality --.

Column 17,
Line 44, after "suitable" delete "pboto-initiators" and insert -- photo-initiators--;
Line 54, after "optionally" delete "crosslinkng" and insert -- cross-linking --.

UNITED STATES PATENT AND TRADEMARK OFFICE
CERTIFICATE OF CORRECTION

PATENT NO.   : 6,316,153 B1
DATED        : November 13, 2001
INVENTOR(S)  : Steven L. Goodman et al.

It is certified that error appears in the above-identified patent and that said Letters Patent is hereby corrected as shown below:

Column 18,
Line 1, after "a" delete "finction" and insert -- function --;
Line 21, after "promote" delete "heaiing" and insert -- healing --;
Line 31, after "ligament" delete "IV";
Line 50, after "components" insert -- . --.

Column 20,
Line 22, after "BSA" (first occurrence) delete "*" and insert -- • --;
Line 22, after "→" delete "(BSSA)" and insert -- (BSA) --;
Line 35, after "Polymerization of" delete "Trimethyloipropane" and insert -- Trimethylolpropane --;
Line 40, after "An" delete "acqlate" and insert -- acrylate --;
Line 58, after "A" delete "polyacrylaride" and insert -- polyacrylamide --.

Column 21,
Line 11, after "BSA" delete "matrixidextran." and insert -- matrix/dextran --;
Line 17, after "1.5" delete "mnicrons," and insert -- microns, --;
Line 26, before "BSA" delete "nm" and insert -- mL --;
Line 61, after "89 micron x" delete "15" and insert -- 1.5 --;
Line 63, after "comprising" delete "$1x_{10}^{-4}$" and insert -- $1x10^{-4}$ --;
Line 66, after "dose =" delete "$2x10^{0}$" and insert -- $2x10^{20}$ --.

Column 23,
Line 20, after "Bengal," delete "erydirosin" and insert --erythrosin --;
Line 33, after "or" delete "cross-lining" and insert -- cross-linking --.

Column 24,
Line 25, after "anions" delete "diatyliodonium" and insert -- diaryliodonium --;
Line 41, after "second" delete "poon" and insert -- portion --;
Line 62, after "controlled" delete "diffisivity" and insert -- diffusivity --.

UNITED STATES PATENT AND TRADEMARK OFFICE
CERTIFICATE OF CORRECTION

PATENT NO. : 6,316,153 B1
DATED : November 13, 2001
INVENTOR(S) : Steven L. Goodman et al.

It is certified that error appears in the above-identified patent and that said Letters Patent is hereby corrected as shown below:

Column 25,
Line 53, after "Bengal," delete "erytlirosin" and insert -- erythrocin --.

Column 26,
Line 26, after "molecules" delete "diffulse" and insert -- diffuse --;
Line 33, after "ions, or" delete "others agents diffuise" and insert -- other agents diffuse --;
Line 42, before "assays;" delete "immunodiffuision" and insert -- immunodiffusion --.

Signed and Sealed this

Seventh Day of February, 2006

JON W. DUDAS
*Director of the United States Patent and Trademark Office*